US011865371B2

(12) United States Patent
Capelli

(10) Patent No.: US 11,865,371 B2
(45) Date of Patent: *Jan. 9, 2024

(54) APPARATUS FOR GENERATING THERAPEUTIC SHOCKWAVES AND APPLICATIONS OF SAME

(75) Inventor: Christopher C. Capelli, Houston, TX (US)

(73) Assignee: The Board of Regents of the University of Texas Syster, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/547,995

(22) Filed: Jul. 12, 2012

(65) Prior Publication Data
US 2013/0018287 A1 Jan. 17, 2013

Related U.S. Application Data

(60) Provisional application No. 61/508,343, filed on Jul. 15, 2011.

(51) Int. Cl.
*A61N 7/00* (2006.01)
*A61B 17/00* (2006.01)

(52) U.S. Cl.
CPC ...... *A61N 7/00* (2013.01); *A61B 2017/00769* (2013.01); *A61N 2007/0034* (2013.01); *A61N 2007/0056* (2013.01)

(58) Field of Classification Search
CPC ............ A61B 17/22004; A61B 17/225; A61B 2017/22008; A61B 17/2251; A61B 18/26;
(Continued)

(56) References Cited

U.S. PATENT DOCUMENTS 2,897,452 A * 7/1959 Southworth ........... H03B 19/03
331/76
3,364,708 A 1/1968 Padberg
(Continued)

FOREIGN PATENT DOCUMENTS

CN 1245410 2/2000
CN 101028525 9/2007
(Continued)

OTHER PUBLICATIONS

Bickle, Abdominal x rays made easy: calcification, STUDENTBMJ vol. 10 Aug. 2002, 272-274.*
(Continued)

*Primary Examiner* — Pascal M Bui Pho
*Assistant Examiner* — Farouk A Bruce
(74) *Attorney, Agent, or Firm* — Mintz, Levin, Cohn, Ferris, Glovsky and Popeo, P.C.

(57) ABSTRACT

Apparatuses and methods to generate high frequency shock waves in a controlled manner. The generated shock waves can be delivered to certain cellular structures of a patient for use in medical and/or aesthetic therapeutic applications. The shock waves can be configured to impose sufficient mechanical stress to the targeted cells of the tissue to rupture the targeted cells. Embodiments of the apparatuses and methods of the present invention provide targeted rupturing of specific cells without damaging side effects such as cavitation or thermal degradation of surrounding non-targeted cells.

20 Claims, 3 Drawing Sheets

(58) Field of Classification Search
CPC .............. A61N 7/00; A61N 2007/0034; A61N 2007/0039
USPC .............................................. 600/439; 601/2
See application file for complete search history.

(56) References Cited

U.S. PATENT DOCUMENTS

| | | | |
|---|---|---|---|
| 3,475,646 A | 10/1969 | Chapman | |
| 3,604,641 A | 9/1971 | Wilson et al. | |
| 3,613,069 A | 10/1971 | Cary | 367/92 |
| 3,735,764 A | 5/1973 | Balev | |
| 3,769,963 A | 11/1973 | Goldman | |
| 3,942,531 A | 3/1976 | Hoff | |
| 4,005,314 A | 1/1977 | Zinn | |
| 4,206,763 A * | 6/1980 | Pedersen | A61B 8/0825 600/445 |
| 4,311,147 A | 1/1982 | Hausler | |
| 4,674,505 A * | 6/1987 | Pauli | G10K 11/30 601/4 |
| 4,715,376 A | 12/1987 | Nowacki et al. | |
| 4,858,597 A | 8/1989 | Kurtze et al. | 601/4 |
| 4,896,673 A | 1/1990 | Rose et al. | 600/439 |
| 4,905,671 A | 3/1990 | Senge et al. | 601/4 |
| 4,928,671 A | 5/1990 | Reichenberger et al. | |
| 4,955,143 A | 9/1990 | Hagelauer | |
| 4,962,752 A * | 10/1990 | Reichenberger | A61B 17/22029 601/4 |
| 4,979,501 A | 12/1990 | Valchanov et al. | 601/2 |
| 5,009,232 A | 4/1991 | Hassler et al. | |
| 5,015,929 A | 5/1991 | Cathignol et al. | 310/335 |
| 5,109,338 A * | 4/1992 | Ermert | G10K 15/043 601/4 |
| 5,146,912 A | 9/1992 | Eizenhoefer | |
| 5,149,406 A | 9/1992 | Mullen et al. | |
| 5,150,713 A | 9/1992 | Okazaki | 600/439 |
| 5,193,527 A | 3/1993 | Schafer | 601/2 |
| 5,195,508 A | 3/1993 | Muller et al. | 601/4 |
| 5,204,820 A | 4/1993 | Strobel et al. | |
| 5,231,976 A | 8/1993 | Wiksell | |
| 5,240,005 A * | 8/1993 | Viebach | 600/472 |
| 5,245,988 A | 9/1993 | Einars et al. | |
| 5,259,368 A | 11/1993 | Wiksell | |
| 5,269,292 A * | 12/1993 | Granz | A61B 17/2258 367/150 |
| 5,284,143 A | 2/1994 | Rattner | 600/427 |
| 5,304,170 A | 4/1994 | Green | |
| 5,304,207 A | 4/1994 | Stromer | |
| 5,327,890 A | 7/1994 | Matura et al. | 600/427 |
| 5,360,447 A | 11/1994 | Koop | |
| 5,374,236 A | 12/1994 | Hassler | |
| 5,393,296 A | 2/1995 | Rattner | 601/2 |
| 5,409,446 A | 4/1995 | Rattner | 601/4 |
| 5,419,327 A | 5/1995 | Rohwedder et al. | 600/439 |
| 5,423,803 A | 6/1995 | Tankovich et al. | |
| 5,435,304 A | 7/1995 | Oppelt et al. | |
| 5,458,652 A | 10/1995 | Uebelacker | 604/4 |
| 5,509,200 A | 4/1996 | Frankeny et al. | |
| 5,529,572 A | 6/1996 | Spector | |
| 5,595,178 A | 1/1997 | Voss et al. | 600/427 |
| 5,618,275 A | 4/1997 | Bock | 604/290 |
| 5,658,239 A | 8/1997 | Delmenico | |
| 5,675,495 A | 10/1997 | Biermann et al. | |
| 5,676,159 A * | 10/1997 | Navis | 128/846 |
| 5,709,676 A | 1/1998 | Alt | |
| 5,722,411 A | 3/1998 | Suzuki | |
| 5,737,462 A | 4/1998 | Whitehouse et al. | |
| 5,790,305 A | 8/1998 | Marcellin-Dibon et al. | |
| 5,827,204 A | 10/1998 | Grandia et al. | 601/2 |
| 6,013,122 A | 1/2000 | Klitzman et al. | 106/31.03 |
| 6,036,661 A | 3/2000 | Schwarze et al. | 601/4 |
| 6,039,694 A | 3/2000 | Larson et al. | |
| 6,058,932 A | 5/2000 | Hughes | |
| 6,080,119 A | 6/2000 | Schwarze et al. | 601/4 |
| 6,096,029 A | 8/2000 | O'Donnell, Jr. | 606/9 |
| 6,113,559 A | 9/2000 | Klopotek | 601/3 |
| 6,113,560 A | 9/2000 | Simnacher | 601/4 |
| 6,123,679 A | 9/2000 | Lafaut et al. | |
| 6,176,839 B1 | 1/2001 | Deluis et al. | 601/2 |
| 6,186,963 B1 | 2/2001 | Schwarze et al. | 601/2 |
| 6,210,329 B1 | 4/2001 | Christmas | |
| 6,217,531 B1 | 4/2001 | Reitmajer | |
| 6,309,355 B1 | 10/2001 | Cain et al. | 600/439 |
| 6,325,769 B1 * | 12/2001 | Klopotek | 601/2 |
| 6,350,245 B1 | 2/2002 | Cimino | 601/2 |
| 6,368,929 B1 | 4/2002 | Hill et al. | 438/312 |
| 6,390,995 B1 | 5/2002 | Ogden et al. | 601/1 |
| 6,450,979 B1 | 9/2002 | Miwa et al. | |
| 6,454,713 B1 | 9/2002 | Ishibashi et al. | 600/439 |
| 6,487,447 B1 | 11/2002 | Weimann et al. | 604/20 |
| 6,491,685 B2 | 12/2002 | Visuri | 606/2.5 |
| 6,500,141 B1 | 12/2002 | Irion et al. | |
| 6,515,842 B1 | 2/2003 | Hayworth et al. | |
| 6,519,376 B2 | 2/2003 | Biagi et al. | 385/7 |
| 6,551,308 B1 | 4/2003 | Muller et al. | |
| 6,666,834 B2 | 12/2003 | Restle et al. | 601/2 |
| 6,755,821 B1 | 6/2004 | Fry | 606/15 |
| 6,800,122 B2 | 10/2004 | Anderson et al. | 106/31.03 |
| 6,905,467 B2 | 6/2005 | Bradley | 600/443 |
| 6,942,663 B2 | 9/2005 | Vargas et al. | |
| 6,948,843 B2 | 9/2005 | Laugharn et al. | 366/127 |
| 6,972,116 B2 | 12/2005 | Brill et al. | 422/186.04 |
| 7,189,209 B1 | 3/2007 | Ogden et al. | |
| 7,250,047 B2 | 7/2007 | Anderson et al. | 606/32 |
| 7,311,678 B2 | 12/2007 | Spector | 601/2 |
| 7,364,554 B2 | 4/2008 | Bolze et al. | 601/2 |
| 7,405,510 B2 | 6/2008 | Kaminski et al. | 310/334 |
| 7,470,240 B2 * | 12/2008 | Schultheiss | A61H 23/0245 601/4 |
| 7,507,213 B2 | 3/2009 | Schultheiss et al. | 601/2 |
| 7,588,547 B2 | 9/2009 | Deem et al. | |
| 7,867,178 B2 | 1/2011 | Simnacher | 601/2 |
| 7,985,189 B1 | 7/2011 | Ogden et al. | 601/2 |
| 7,988,631 B2 | 8/2011 | Bohris | 600/439 |
| 8,057,408 B2 * | 11/2011 | Cain et al. | 601/2 |
| 8,088,073 B2 | 1/2012 | Simnacher et al. | 600/472 |
| 8,092,401 B2 | 1/2012 | Schultheiss | 601/2 |
| 8,102,734 B2 | 1/2012 | Sliwa et al. | 367/140 |
| 8,235,899 B2 | 8/2012 | Hashiba | 600/437 |
| 8,257,282 B2 | 9/2012 | Uebelacker et al. | 601/4 |
| 8,298,162 B2 | 10/2012 | Del Giglio | |
| 8,323,220 B2 * | 12/2012 | Babaev | 601/2 |
| 8,343,420 B2 | 1/2013 | Cioanta et al. | |
| 8,357,095 B2 | 1/2013 | Anderson et al. | 600/441 |
| 8,672,721 B2 | 3/2014 | Camilli | |
| 8,684,970 B1 | 4/2014 | Koyfman | |
| 2002/0009015 A1 * | 1/2002 | Laugharn et al. | 366/108 |
| 2002/0048218 A1 * | 4/2002 | Sugimoto | F25B 9/145 367/140 |
| 2002/0193831 A1 | 12/2002 | Smith | |
| 2003/0167964 A1 | 9/2003 | Anderson et al. | |
| 2003/0233045 A1 | 12/2003 | Vaezy et al. | |
| 2004/0006288 A1 | 1/2004 | Spector et al. | |
| 2004/0181219 A1 | 9/2004 | Goble et al. | |
| 2005/0015023 A1 * | 1/2005 | Ein-Gal | A61B 17/22004 601/2 |
| 2005/0137656 A1 | 6/2005 | Malak | |
| 2005/0150830 A1 * | 7/2005 | Laugharn, Jr. | B01F 11/02 210/634 |
| 2006/0036168 A1 | 2/2006 | Liang et al. | |
| 2006/0064082 A1 | 3/2006 | Bonutti | |
| 2006/0094988 A1 * | 5/2006 | Tosaya | A61H 23/0245 601/2 |
| 2006/0158956 A1 * | 7/2006 | Laugharn, Jr. | B01F 11/02 366/127 |
| 2006/0173388 A1 | 8/2006 | Ginter et al. | |
| 2006/0184071 A1 | 8/2006 | Klopotek | |
| 2006/0200116 A1 | 9/2006 | Ferren et al. | |
| 2006/0211958 A1 | 9/2006 | Rosenberg et al. | |
| 2007/0016112 A1 | 1/2007 | Schultheiss et al. | |
| 2007/0038060 A1 | 2/2007 | Cerwin et al. | |
| 2007/0049829 A1 | 3/2007 | Kaminski et al. | 600/459 |
| 2007/0055180 A1 | 3/2007 | Deem et al. | |
| 2007/0065420 A1 | 3/2007 | Johnson | |

(56) References Cited

U.S. PATENT DOCUMENTS

| | | |
|---|---|---|
| 2007/0135755 A1 | 6/2007 | Bernabei et al. |
| 2007/0198068 A1 | 8/2007 | Chan et al. |
| 2007/0219760 A1 | 9/2007 | Yang et al. |
| 2007/0239072 A1* | 10/2007 | Schultheiss ............ A61N 7/00 601/2 |
| 2007/0239082 A1 | 10/2007 | Schultheiss et al. |
| 2007/0239084 A1 | 10/2007 | Voss |
| 2007/0249939 A1 | 10/2007 | Gerbi et al. |
| 2008/0009774 A1 | 1/2008 | Capelli et al. ................ 601/3 |
| 2008/0009885 A1 | 1/2008 | Del Giglio ................ 606/128 |
| 2008/0021447 A1 | 1/2008 | Davison et al. |
| 2008/0071198 A1 | 3/2008 | Ogden et al. |
| 2008/0107744 A1 | 5/2008 | Chu ............................ 424/489 |
| 2008/0132810 A1 | 6/2008 | Scoseria et al. |
| 2008/0146971 A1* | 6/2008 | Uebelacker ...... A61B 17/22004 601/4 |
| 2008/0154157 A1 | 6/2008 | Altshuler et al. |
| 2008/0183200 A1* | 7/2008 | Babaev ...................... 606/169 |
| 2008/0194967 A1 | 8/2008 | Sliwa et al. .................. 600/472 |
| 2008/0195003 A1 | 8/2008 | Sliwa et al. .................... 601/3 |
| 2008/0262483 A1* | 10/2008 | Capelli ................. A61N 7/02 606/9 |
| 2008/0269163 A1 | 10/2008 | Sostaric |
| 2008/0269608 A1 | 10/2008 | Anderson et al. ............ 600/439 |
| 2008/0319356 A1 | 12/2008 | Cain et al. |
| 2009/0018472 A1 | 1/2009 | Soltani et al. |
| 2009/0062644 A1* | 3/2009 | McMorrow ............. A61B 8/08 600/437 |
| 2009/0275832 A1 | 11/2009 | Gelbart et al. |
| 2010/0049098 A1 | 2/2010 | Shalgi et al. |
| 2010/0076349 A1 | 3/2010 | Babaev ............... 601/2 |
| 2010/0082019 A1 | 4/2010 | Neev |
| 2010/0087899 A1 | 4/2010 | Erez et al. .................. 607/101 |
| 2010/0168575 A1 | 7/2010 | Hashiba ....................... 600/443 |
| 2010/0204617 A1 | 8/2010 | Ben-Ezra ........................ 601/2 |
| 2010/0208467 A1 | 8/2010 | Dross |
| 2010/0249768 A1 | 9/2010 | Avramenko et al. |
| 2010/0274161 A1 | 10/2010 | Azhari et al. |
| 2010/0280420 A1 | 11/2010 | Barthe et al. |
| 2010/0331741 A9 | 12/2010 | Cioanta et al. ................... 601/2 |
| 2011/0034832 A1 | 2/2011 | Cioanta et al. ................... 601/1 |
| 2011/0087157 A1 | 4/2011 | Cioanta et al. ................. 604/22 |
| 2011/0319793 A1* | 12/2011 | Hynynen ................. A61N 7/02 601/2 |
| 2012/0157892 A1 | 6/2012 | Reitmajer et al. |
| 2012/0167174 A1 | 6/2012 | Saxena et al. |
| 2012/0253240 A1 | 10/2012 | Uebelacker et al. |
| 2012/0253416 A1 | 10/2012 | Erez et al. ........................ 607/3 |
| 2012/0271169 A1* | 10/2012 | Coussios ................. A61N 7/02 600/439 |
| 2012/0310232 A1 | 12/2012 | Erez ................ 606/33 |
| 2012/0323147 A1 | 12/2012 | Scheirer |
| 2012/0330288 A1 | 12/2012 | Clementi et al. |
| 2013/0018287 A1 | 1/2013 | Capelli |
| 2013/0046179 A1 | 2/2013 | Humayun |
| 2013/0046207 A1 | 2/2013 | Capelli |
| 2013/0345600 A1 | 12/2013 | Katragadda et al. |
| 2014/0005576 A1 | 1/2014 | Adams |
| 2014/0094718 A1 | 4/2014 | Feldman |
| 2014/0228820 A1 | 8/2014 | Blaskowski et al. |
| 2014/0243715 A1 | 8/2014 | Cioanta et al. |
| 2014/0243847 A1 | 8/2014 | Hakala et al. |
| 2014/0257144 A1 | 9/2014 | Capelli et al. |
| 2014/0276693 A1 | 9/2014 | Altshuler et al. |
| 2014/0276722 A1 | 9/2014 | Parihar et al. |
| 2014/0277219 A1 | 9/2014 | Nanda |
| 2014/0378740 A1 | 12/2014 | Wagner et al. |
| 2015/0105702 A1 | 4/2015 | Wagner et al. |
| 2015/0126913 A1 | 5/2015 | Jurna et al. |
| 2015/0217111 A1 | 8/2015 | Stevenson et al. |
| 2016/0016013 A1 | 1/2016 | Capelli et al. |
| 2016/0067139 A1 | 3/2016 | Katragadda et al. |
| 2016/0166837 A1 | 6/2016 | Strommer et al. |
| 2016/0262778 A1 | 9/2016 | Du |
| 2016/0271419 A1 | 9/2016 | Varghese et al. |
| 2018/0116905 A1 | 5/2018 | Capelli et al. |
| 2018/0221688 A1 | 8/2018 | Cioanta et al. |

FOREIGN PATENT DOCUMENTS

| | | |
|---|---|---|
| CN | 101146574 | 3/2008 |
| CN | 101155614 | 4/2008 |
| CN | 100530868 | 8/2009 |
| CN | 101610736 | 12/2009 |
| CN | 102057422 | 5/2011 |
| CN | 102247661 | 11/2011 |
| CN | 105209117 | 12/2015 |
| CN | 105246419 | 1/2016 |
| DE | 3150430 | 7/1983 |
| DE | 3710371 | 10/1988 |
| DE | 60008898 | 1/2005 |
| DE | 102007046902 | 4/2009 |
| EP | 0008647 | 3/1980 |
| EP | 0243650 | 11/1987 |
| EP | 0322473 | 7/1989 |
| EP | 0326620 | 8/1989 |
| EP | 2964326 | 1/2016 |
| EP | 3626307 | 3/2020 |
| FR | 2605874 | 5/1988 |
| GB | 2303552 | 2/1997 |
| JP | 53-111689 | 9/1978 |
| JP | S61-293447 | 12/1986 |
| JP | S 61-293447 | 12/1986 |
| JP | 62-192150 | 8/1987 |
| JP | S 63-023775 | 2/1988 |
| JP | S63-111852 A | 5/1988 |
| JP | S63-183050 | 7/1988 |
| JP | S 63-183050 | 7/1988 |
| JP | 6-7365 | 1/1994 |
| JP | H067365 | 1/1994 |
| JP | H 06-505648 | 6/1994 |
| JP | H06-505648 | 6/1994 |
| JP | 8-140984 | 6/1996 |
| JP | 08140984 A * | 6/1996 |
| JP | H 08140984 | 6/1996 |
| JP | 8-194079 | 7/1996 |
| JP | 1996-222472 | 8/1996 |
| JP | H0-8224253 | 9/1996 |
| JP | 9-103434 | 4/1997 |
| JP | H09103434 | 4/1997 |
| JP | H 10192289 | 7/1998 |
| JP | H 10328192 | 12/1998 |
| JP | 2003-500126 | 1/2003 |
| JP | 2004526507 | 9/2004 |
| JP | 2005514142 | 5/2005 |
| JP | 2007-000218 | 1/2007 |
| JP | 2009506870 | 2/2009 |
| JP | 2009508649 A | 3/2009 |
| JP | 2009-518126 | 4/2009 |
| JP | 2009-527262 | 7/2009 |
| JP | 2009543614 | 12/2009 |
| JP | 2012-516170 | 7/2012 |
| JP | 2013537559 | 10/2013 |
| JP | 2014-507990 | 4/2014 |
| JP | 2014525782 | 10/2014 |
| JP | 2016/523602 | 8/2016 |
| JP | 2017-500078 | 1/2017 |
| KR | 101886863 | 8/2018 |
| RU | 2121812 C1 | 11/1998 |
| RU | 2151559 C1 | 6/2000 |
| RU | 2600504 C1 | 10/2016 |
| TW | 200604017 | 2/2006 |
| TW | I 292341 | 1/2008 |
| TW | I 350249 | 10/2011 |
| WO | WO 91/10227 | 7/1991 |
| WO | WO 2000/071207 | 11/2000 |
| WO | WO 2002/030256 | 4/2002 |
| WO | WO 2004/080147 | 9/2004 |
| WO | WO 2007/067563 | 6/2007 |
| WO | WO 2007/088546 | 8/2007 |
| WO | WO/07/146988 | 12/2007 |
| WO | WO 2008/052198 | 5/2008 |
| WO | WO 2008/074005 | 6/2008 |

(56) References Cited

FOREIGN PATENT DOCUMENTS

| WO | WO 2008/137942 | 11/2008 |
|---|---|---|
| WO | WO 2010/086301 | 8/2010 |
| WO | WO 2011/077466 | 6/2011 |
| WO | WO/11/091020 | 7/2011 |
| WO | WO 2011/091020 | 7/2011 |
| WO | WO 2012/107830 | 8/2012 |
| WO | WO 2013/012724 | 1/2013 |
| WO | WO 2010/122517 | 8/2014 |
| WO | WO 2014/138582 | 9/2014 |
| WO | WO 2014/191263 | 12/2014 |
| WO | WO 2015/176001 | 11/2015 |
| WO | WO 2017/165595 | 9/2017 |
| WO | WO 2018/136514 | 7/2018 |

OTHER PUBLICATIONS

Fernando, A Nonlinear Computational Method for the Propagation of Shock Waves in Aero-engine Inlets Towards a new Model for Buzz-saw Noise Prediction. 15th AIAA/CEAS Aeroacoustics Conference (30th AIAA Aeroacoustics Conference) May 11-13, 2009, p. 1-18.*

Reichenberger, Electromagnetic Acoustic Source for Extracorporeal Geneartion of Shock Waves in Lithotripsy, Siemens Forsch, 1986, 187-194.*

Falco, "Single-point Nonlinearity Indicators for the Propagation of High-amplitude Acoustic Signals," Ph.D. Thesis, Graduate Program in Acoustics, , The Pennsylvania State University, University Park, PA, May 2007.*

Baumler et al., Q-Switch Laser and Tattoo Pigments: First Results of the Chemical and Photophysical Analysis of 41 Compounds, Lasers in Surgery and medicine 26:13-21 (2000), pp. 13-21.

Chen et al., "The disappearance of ultrasound contrast bubbles: Observations of bubble dissolution and Cavitation nucleation", Ultrasound in Med. & Biol., vol. 28, No. 6, pp. 793-803, 2002.

Eisenmenger, W. et al., The First Clinical Results of "Wide-Focus and Low-Pressure ESWL" Ultrasound in Med. & Biol., vol. 28, No. 6, pp. 769-774, 2002.

Eisenmenger, Wolfgang, "The Mechanisms of Stone Fragmentation in ESWL", Ultrasound in Med. & Biol., vol. 27, No. 5, pp. 683-693, 2001.

Ho et al., "Laser-Tattoo Removal—A Study of the Mechanism and the Optimal Treatment Strategy via Computer Simulations", Lasers in Surgery and medicine 30:389-391 (2002).

International Preliminary Report on Patentability of PCT/US2011/021692, dated Jul. 24, 2012, 6 pages.

Kuperman-Beade et al., "Laser Removal of Tattoos", Am J Clin Dermatol 2001: 2(1):21-25.

Kuzmin et al., "Ultrasonic Cavitational Chemical Technologies", XI Session of the Russian Acoustical Society, Moscow, Nov. 19-23, 2001.

Ng et al., "Therapeutic Ultrasound: Its Application in Drug Delivery", Medicinal Research Reviews, vol. 22, No. 2, 204-223, 2002.

Ogden et al., Principles of Shcok Wave Therapy, Clinical Orthopaedics and Related Research, No. 387, pp. 8-17.

Ross et al., "Comparison of Responses of Tattoos to Picosecond and Nanosecond Q-Switched Neodymium: YAG Lasers" ARCH Dermatol/vol. 134, Feb. 1998, pp. 167-171.

Search Report and Written Opinion in PCT/US12/46674 dated Oct. 26, 2012.

Solis et al., "Experimental Nonsurgical Tattoo Removal in a Guinea Pig Model with Topical Imiquimod and Tretinoin", Dermatol Surg. 2002, 28:83-87.

Timko et al., "In Vitro Quantitative Chemical Analysis of Tattoo Pigments", ARCH Dermatol/vol. 137, Feb. 2001, pp. 143-147.

Varma, S., "Tattoo Ink Darkening of a yellow Tattoo after Q-Switched Laser Treatment", 2002 Blackwell Science Ltd., Clinical and Experimental Dermatology, 27, 461-463.

Wolfrum et al., "Shock wave induced interaction of microbubbles and boundaries", Physics of Fluids, vol. 15, No. 10, Oct. 2003, pp. 2916-2922.

International Search Report and Written Opinion issued in PCT/US2011/021692, dated Sep. 20, 2011.

International Search Report and Written Opinion issued in PCT/US2012/046674, dated Oct. 26, 2012.

Sheth and Pandya, "Melsama: A comprehensive update (Part I)", Journal of the American Academy of Dermatology, 65:689-697, 2011.

Sheth and Pandya, "Melsama: A comprehensive update (Part II)", Journal of the American Academy of Dermatology, 65:699-714, 2011.

Kuhn et al., "Impact of extracorporeal shock waves on the human skin with cellulite: A case study of an unique instance", Clinical Interventions of Aging, 3(1):201-210, 2008.

Patent Examination Report No. 1 in Australian Patent Application No. 2012284323 dated Jan. 9, 2014.

Office Action in Japanese Patent Application No. 2012-550085 dated Oct. 2, 2014.

Extended European Search Report in European Application No. 12814465.6 dated Feb. 24, 2015.

Office Action in Chinese Patent Application No. 201180011442.0 dated Mar. 2, 2015.

Office Action in Chinese Patent Application No. 201280041817.2 dated Feb. 4, 2015.

Office Action in Japanese Patent Application No. 2012-550085 dated Jun. 10, 2015.

Examination Reporting issued in Australian Patent Application No. 2016277677, dated Dec. 11, 2017.

Office Action Issued in Corresponding Australian Patent Application No. 2019200537, dated Mar. 3, 2020.

Office Action Issued in Corresponding Indian Patent Application No. 334/DELNP/2014, dated Jan. 29, 2020.

Office Action issued in Corresponding European Application No. 11735097.5, dated Nov. 15, 2018.

Office Action Issued in Corresponding Korean Application No. 10-2014-7003927, dated Dec. 26, 2018.

Burov, et al., "Nonlinear Ultrasound: Breakdown of Microscopic Biological Structures and Nonthermal Impact on Malignant Tumor," Doklady Biochemistry and Biophysics, 383(3), pp. 101-104. (2002).

Decision on Grant Patent for Invention in Russian Application No. 2012135506/14(057136) dated May 12, 2014.

Delius, et al., "Biological Effects of Shock Waves: Kidney Haemorrhage by Shock Waves in Dogs—Administration Rate Dependence," Ultrasound Med Biol., 14(8), 689-694, 1988.

Gillitzer, et al., "Low-Frequency Extracorporeal Shock Wave Lithotripsy Improves Renal Pelvic Stone Disintegration an a Pig Model," BJU Int, 176, 1284-1288, 2009.

International Search Report and Written Opinion Issued for PCT/US2011/021692, dated Sep. 20, 2011.

Liu, et al., "Optimized Design of LED Freeform Lens for Uniform Circular Illumination," Journal of Zhejiang University-Science C, Computer & Electron, 13(12), 929-936, 2012.

Madbouly, et al., "Slow Versus Fast Shock Wave Lithotripsy Rate for Urolithiasis: A Prospective Randomized Study," The Journal of Urology, 173, 127-130, 2005.

Nana, et al., "Application of the Multiple Low-Energy Q-Switched Laser for the Treatment of Tattoos in 21 Cases," China Aesthetic Medicine, 4(21), 621-622, 2012. (English Abstract).

Notice of Allowance in Canadian Application No. 2,787,528 dated Apr. 9, 2014.

Notice of Final Rejection in Korean Application No. 10-2012-7021437 dated Jun. 26, 2014.

Office Action Issued in Corresponding Japanese Patent Application No. 2017-133546 with English Translation, dated Jun. 4, 2018.

Office Communication in Chinese Application No. 201180011442.0 dated Jul. 3, 2014.

Patent Examination Report No. 2 in Australian Patent Application No. 2011207601 dated Apr. 4, 2014.

Vogel, et al., "Shock Wave Emission and Cavitation Bubble Generation by Picosecond and Nanosecond Optical Breakdown in Water," J. Acoust. Soc Am. 100(1), Jul. 1996.

(56) References Cited

OTHER PUBLICATIONS

Boxman, et al., "Handbook of Vacuum Arc Science and Technology: Fundamentals and Applications," Park Ridge, New Jersey: Noyes Publications, pp. 316-319, 1995.
Extended European Search Report Issued in Corresponding European Patent Application No. 20153807.1, dated Jun. 9, 2020.
International Preliminary Report on Patentability Issued in Corresponding PCT Application No. PCT/US2017/042122, dated Jan. 22, 2019.
International Search Report and Written Opinion Issued in Corresponding PCT Application No. PCT/US2017/042122, dated Jan. 9, 2018.
International Search Report and Written Opinion Issued in Corresponding PCT Application No. PCT/US14/21746, dated Sep. 12, 2014.
Office Action Issued in Corresponding Japanese Patent Application No. 2019-012062, dated Jun. 16, 2020.
Partial Supplementary Search Report Issued in Corresponding European Patent Application No. EP18754679.1, dated Jul. 29, 2020.
Schmitz, et al., "Treatment of Chronic Plantar Fasciopathy with Extracorporeal Shock Waves (Review)," *Journal of Orthopaedic Surgery and Research*, 8(1); 31, 2013.
Ushakov, et al., "Impulse Breakdown of Liquids," New York, New York: Springer. 2007.
Office Action Issued in Chinese Patent Application No. 201910058064, dated Feb. 8, 2021.
Office Action Issued in Chinese Patent Application No. 201910058064, dated Oct. 25, 2021.
Teng, J., "Ultrasound: an alternative solution for removing tattoos." *Massachusetts Institute of Technology*, pp. 3-6, 12-65; 2005.
International Search Report and Written Opinion Issued in Corresponding PCT Application No. PCT/US2020/026425 dated Sep. 2, 2020.
Office Action and Search Report issued in Corresponding Chinese Application No. 201780056472.0, dated Jan. 19, 2022 (English Translation provided).
Office Action issued in Australian Patent Application No. 2021201670, dated Jun. 20, 2022.
Office Action issued in U.S. Appl. No. 16/478,611, dated Jun. 30, 2022.
Troilius, "Effective Treatment of traumatic Tattoos with a Q-switched Nd:YAG laser," Lasers Surg. Med., 22:103-108, 1998.
Carlberg, "Upgrading from Stepper to Servo," Yaskawa America Inc., pp. 1-7, 2011.
Manousakas et al., "Development of a system of automatic gap-adjusted electrodes for shock wave generators," Review of Scientific Instruments, 75(11):4811-4819, 2004.
Office Action issued in U.S. Appl. No. 16/478,611, dated Oct. 31, 2022.
Notice of Allowance issued in U.S. Appl. No. 17/648,790, dated Feb. 28, 2023.
Office Communication issued in Japanese Patent Application No. 2018-550349, dated Mar. 7, 2023. (English translation).
Official Action issued in Japanese Patent Application No. 2019-544631, dated Sep. 16, 2022.
Official Action issued in U.S. Appl. No. 16/486,920, dated Sep. 14, 2022.
English translation of Office Action issued in Korean Patent Application No. 10-2019-7005043 dated Sep. 28, 2022.
Office Action issued in U.S. Appl. No. 16/087,976 dated Oct. 13, 2022.
English translation of Office Action issued in Japanese Patent Application No. 2021-184610, dated Nov. 18, 2022.
Office Action issued in Australian Patent Application No. 2018221251, dated Nov. 10, 2022.
Notice of Preliminary Rejection in Korean Application No. 10-2012-7021437 dated Oct. 24, 2013.
Office Communications issued in U.S. Appl. No. 16/319,509, dated Apr. 10, 2023.
Brooks LA, Zander AC, Hansen CH, (2005). "Investigation into the feasibility of using a parametric array control source in an active noise control system," Proceedings of Acoustics 2005, Nov. 9-11, 2005. Australian Acoustical Society, pp. 39-45.

* cited by examiner

APPARATUS FOR GENERATING THERAPEUTIC SHOCKWAVES AND APPLICATIONS OF SAME

CROSS-REFERENCE TO RELATED APPLICATIONS

This application claims priority to U.S. provisional application Ser. No. 61/508,343, filed on Jul. 15, 2011, the disclosure of which is incorporated by reference herein in its entirety.

TECHNICAL FIELD

Embodiments of the present invention relate generally to therapeutic uses of shock waves. More particularly, but not by way of limitation, embodiments of the present invention relate to an apparatus for generating therapeutic shock waves (shock waves with therapeutic uses) and applications of same.

BACKGROUND

Shockwaves have been used in certain medical and aesthetic therapies. For instance, shockwaves have been used in the form of extracorporeal lithotripsy, in which pulses may be used to form shock fronts to fragment renal calculi. The shockwave source in lithotripsy is typically generated by the discharge of electric energy between test electrodes.

Shockwaves in medical therapy may originate from other sources. For example, U.S. Pat. No. 6,325,769, by Peter J. Klopotek, describes applying a focused ultrasound beam to a region of human skin to generate a shockwave to treat wrinkles. A problem with the generation of shockwaves as described by Klopotek is that it is not predictable.

As described by Klopotek, the shockwaves form as they travel through the skin because of the nonlinear nature of the skin tissue. The formation of a shockwave is dependent on the frequency and amplitude of the acoustic waves. Additionally, the formation of a shockwave is dependent on the medium in which the wave is traveling. Depending on the frequency, amplitude and media, the distance at which a shockwave forms from the transducer head is relatively large and can vary drastically depending on the type of tissue. Available methods do not provide for creating consistent high-frequency shockwaves suitable for therapy.

SUMMARY

Certain embodiments of the apparatus described in this disclosure allow for generating of high frequency shock waves from acoustic waves.

Certain embodiments of the method described in this disclosure deliver the generated high frequency shock waves to a patient's tissue to selectively rupture cellular structures with certain properties, such as particle-containing cellular structures.

Certain embodiments of the apparatus described in this disclosure have particular applications in removing tattoos or other skin markings and provide certain advantages over current tattoo removal techniques.

Advantages provided by certain embodiments of the apparatus and method described in this disclosure include removal of tattoos or other skin markings may be removed or diminished with little if any pain to the patient. Further, this can be done with minimal damage or destruction of surrounding tissues.

According to certain aspects, the present disclosure includes embodiments of methods and apparatuses for directing shock waves to the cells of a patient (e.g., a mammal).

Some embodiments of the present methods comprise: directing shock waves to cells of a patient; where the shock waves are configured to cause particles to rupture one or more of the cells.

Some embodiments of the present methods comprise: providing an apparatus (e.g., comprising: an acoustic-wave generator configured to emit acoustic waves having at least one frequency between 1 MHz and 1000 MHz; a shockwave housing coupled to the acoustic-wave generator; and a shockwave medium disposed in the shockwave housing; where the apparatus is configured such that if the acoustic-wave generator emits acoustic waves then at least some portion of the acoustic waves will travel through the shockwave medium and form shock waves); actuating the apparatus to form shock waves configured to cause particles within a patient to rupture one or more cells of the patient; and directing the shock waves to cells of a patient such that the shock waves cause particles to rupture one or more of the cells.

In some embodiments, the shockwave medium is unitary with the shockwave housing. In some embodiments, the shockwave housing defines a chamber, and where the shockwave medium is disposed in the chamber. In some embodiments, the shockwave medium is configured such that in the presence of acoustic waves from the acoustic-wave generator the shockwave medium will exhibit nonlinear properties. In some embodiments, the shockwave medium comprises one or more of: bubbles, solid particles, or a combination of bubbles and solid particles.

In some embodiments, the shockwave housing defines a chamber having an input end coupled to the acoustic-wave generator and an outlet end extending from the acoustic-wave generator, and where the shockwave housing includes an end cap covering the outlet end of the chamber. In some embodiments, the end cap is configured such that attenuation of a shockwave exiting the end cap will be less than twenty percent. In some embodiments, the shockwave housing is configured such that if acoustic waves are incident on the shockwave housing from within the shockwave chamber, then the shockwave housing will reflect at least some portion of the incident acoustic waves back into the shockwave chamber. In some embodiments, the distance from the acoustic-wave generator to the outlet end of the chamber is greater than or equal to:

$$L = \frac{c_0^3 \rho_0}{\epsilon \omega P_0} = \frac{\lambda}{2\pi M_\omega}$$

where $\epsilon$=nonlinear parameter of shockwave medium; $\omega$=frequency of acoustic wave; $\rho_0$=density of the shockwave medium; $\lambda$=wavelength of acoustic wave; $c_0$=velocity of sound in the shockwave medium; $P_0$=pressure amplitude in shockwave medium; and $M_\omega$=acoustic mach number=$P_0 \div (c_0^2 \rho_0)$. In some embodiments, the acoustic-wave generator comprises an ultrasound head.

In some embodiments, the apparatus comprises: a controller coupled to the acoustic-wave generator and configured to actuate the acoustic-wave generator to emit acoustic waves. In some embodiments, the controller is configured to adjust the acoustic-wave generator to vary at least one of the amplitude and frequency of acoustic waves emitted from the acoustic-wave generator. In some embodiments, the controller is configured to actuate the acoustic-wave generator to continuously emit acoustic waves for a period of time. In some embodiments, the controller is configured to actuate the acoustic-wave generator to emit acoustic waves in an intermittent on-off sequence.

In some embodiments, the acoustic-wave generator is a first acoustic-wave generator, and where the apparatus comprises: a second acoustic-wave generator configured to emit acoustic waves having at least one frequency between 1 MHz and 1000 MHz; where the shockwave housing is also coupled to the second acoustic-wave generator; where the apparatus is configured such that if the second acoustic-wave generator emits acoustic waves then at least some portion of the acoustic waves will travel through the shockwave medium and form shock waves; and where the controller is also coupled to the second acoustic-wave generator and configured to actuate second the acoustic-wave generator to emit acoustic waves. In some embodiments, the controller is configured to actuate the first and second acoustic-wave generators such that the acoustic waves that are emitted from the second acoustic-wave generator are out-of-phase from the waves that are emitted from the first acoustic-wave generator.

In some embodiments, the apparatus is configured to fit within a box having a length of 3 feet, a width of 2 feet, and a height of 2 feet. In some embodiments, the apparatus is configured to fit within a box having a length of 2 feet, a width of 1 foot, and a height of 1 foot.

In some embodiments, the particles comprise non-natural particles. In some embodiments, the particles comprise tattoo pigment. In some embodiments, at least a portion of the tattoo pigment is disposed between skin cells of the patient. In some embodiments, at least a portion of the tattoo pigment is disposed within skin cells of the patient. In some embodiments, the particles comprise an element with an atomic number of less than 82. In some embodiments, the particles comprise gold. In some embodiments, the particles comprise one or more materials selected from the group consisting of: titanium dioxide, iron oxide, carbon, and gold. In some embodiments, the particles comprise pigment particles having one or more materials selected from the group consisting of: titanium, aluminum, silica, copper, chromium, iron, carbon, and oxygen. In some embodiments, the particles have a mean diameter of less than 1000 nm. In some embodiments, the particles have a mean diameter of less than 500 nm. In some embodiments, the particles have a mean diameter of less than 100 nm. In some embodiments, the particles comprise one or more materials selected from the group consisting of: silk, silk fibron, carbon nanotubes, liposomes, and gold nanoshells.

In some embodiments, the particles comprise natural particles. In some embodiments, the particles comprise crystalline micro-particles. In some embodiments, the crystalline micro-particles are disposed in the musculoskeletal system of the patient. In some embodiments, the particles comprise one or more materials selected from the group consisting of: urate crystals, calcium-containing crystals, and hyroxyapatite crystals. In some embodiments, the particles comprise dirt or debris disposed in a pore of the patient's skin. In some embodiments, the particles comprise keratin protein disposed in the patient's skin. In some embodiments, the one or more shockwaves are configured to have substantially no lasting effect on cells in the absence of particles.

In some embodiments, the present methods comprise: directing particles to a position at or near the cells prior to directing shockwaves to the cells. In some embodiments, directing particles comprises injecting into the patient a fluid suspension that includes the particles. In some embodiments, the fluid suspension comprises saline. In some embodiments, the fluid suspension comprises hyaluronic acid.

In some embodiments, the present methods comprise: directing a chemical or biological agent to a position at or near the cells. In some embodiments, directing a chemical or biological agent is performed by delivering the chemical or biological agent transdermally. In some embodiments, directing a chemical or biological agent is performed by delivering the chemical or biological agent systemically. In some embodiments, directing a chemical or biological agent is performed by injecting the chemical or biological agent into the patient. In some embodiments, the chemical or biological agent comprises one or more of a chelator or ethylenediaminetetraacetic acid (EDTA). In some embodiments, the chemical or biological agent comprises one or more of an immune modulator or Imiquimod. In some embodiments, directing a chemical or biological agent is performed before directing the one or more shockwaves. In some embodiments, directing a chemical or biological agent is performed after directing the one or more shockwaves. In some embodiments, directing a chemical or biological agent is performed simultaneously with directing the one or more shockwaves.

In some embodiments, the present methods comprise: identifying target cells of the patient to be ruptured; where identifying target cells is performed prior to directing the shock waves. In some embodiments, the target cells comprise a tattoo. In some embodiments, the target cells comprise musculoskeletal cells comprising crystalline micro-particles. In some embodiments, the target cells comprise one or more skin maladies selected from the group consisting of: blackheads, cysts, pustules, papules, and whiteheads. In some embodiments, the target cells comprise hair follicles and contain keratin protein. In some embodiments, the target cells comprise dental follicles and contain enamel. In some embodiments, the target cells comprise cancer cells.

In some embodiments, the present methods comprise: directing a beam of light from a Q-switched laser at the cells. In some embodiments, directing the one or more shockwaves and directing the beam of light are performed in an alternating sequence.

In some embodiments, directing the one or more shockwaves comprises focusing the one or more shockwaves at a specific region of tissue comprising the cells. In some embodiments, the region of tissue is at a depth beneath the patient's skin.

Some embodiments of the present apparatuses for generating therapeutic shock waves, comprise: an acoustic-wave generator configured to emit acoustic waves having at least one frequency between 1 MHz and 1000 MHz; a shockwave housing coupled to the acoustic-wave generator; and a shockwave medium disposed in the shockwave housing; where the shockwave housing is configured to be removably coupled to the acoustic wave generator such that the acoustic-wave generator can be actuated to emit acoustic waves that will travel through the shockwave medium and form one or more shock waves. In some embodiments, the shockwave housing includes an input end configured to be coupled to the acoustic-wave generator, and an outlet end extending from the input end. In some embodiments, the shockwave housing comprises a shockwave medium within the shockwave housing. In some embodiments, the shockwave medium is unitary with the shockwave housing.

Some embodiments of the present methods comprise: providing an embodiment of the present apparatuses; and actuating the apparatus to form shock waves configured to cause particles within a patient to rupture one or more cells of the patient. Some embodiments comprise: directing the shock waves to cells of a patient such that the shock waves cause particles to rupture one or more of the cells. Some embodiments comprise: coupling the shockwave housing to the acoustic wave actuator prior to actuating the apparatus.

Any embodiment of any of the present systems and/or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

According to another aspect, there is provided a method comprising the steps of: providing a plurality of acoustic waves having at least one frequency of at least 1 MHz; propagating at least a portion of the acoustic waves through a shockwave medium configured to exhibit nonlinear properties in the presence of the propagated acoustic waves to generate a plurality of shock waves; and delivering at least a portion of said plurality of shock waves to at least one cellular structure comprising at least one region of heterogeneity; and rupturing the at least one cellular structure with the continued delivery of said plurality of shock waves. In one embodiment, the at least one region of heterogeneity comprises an effective density greater than an effective density of the at least one cellular structure.

According to yet another aspect, there is an apparatus comprising: an acoustic-wave generator configured to emit acoustic waves having at least one frequency between about 1 MHz and about 1000 MHz; a shockwave medium coupled to the acoustic-wave generator; and wherein the apparatus is configured to propagate at least a portion of the emitted acoustic waves through the shockwave medium to form shock waves; and wherein the formed shock waves are configured to rupture to at least one cellular structure comprising at least one region of heterogeneity. In one embodiment, the shockwave medium has a Goldberg number of greater than or equal to 1 wherein the Goldberg number is determined by dividing the length of the shockwave medium by the absorption length of the shockwave medium, where the absorption length is defined at least by the reciprocal of the attenuation coefficient of the shockwave medium. In another embodiment, the at least one region of heterogeneity comprises an effective density greater than an effective density of the at least one cellular structure.

Other advantages and features will be apparent from the following detailed description when read in conjunction with the attached drawings. The foregoing has outlined rather broadly the features and technical advantages of the embodiments of the present invention so the detailed description that follows may be better understood. Additional features and advantages of the embodiments of the present invention will be described hereinafter which form the subject of the claims of the present disclosure. It should be appreciated by those skilled in the art that the conception and specific embodiment disclosed may be readily utilized as a basis for modifying or designing other structures for carrying out the same purposes disclosed here. It should also be realized by those skilled in the art that such equivalent constructions do not depart from the spirit and scope of the embodiments of the present invention as set forth in the appended claims. The novel features which are believed to be characteristic of the present invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the embodiments described herein.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those one or more steps. For example, in a method that comprises directing shock waves to cells of a patient, the method includes the specified step but is not limited to having only that step. Likewise, an apparatus that "comprises," "has," "includes" or "contains" one or more elements possesses those one or more elements, but is not limited to possessing only those elements. For example, in an apparatus that comprises an acoustic-wave generator and a shockwave housing coupled to the acoustic-wave generator, the apparatus includes the specified elements but is not limited to having only those elements. For example, such an apparatus could also include a shockwave medium disposed in the shockwave housing. Further, a device or structure that is configured in a certain way is configured in at least that way, but it can also be configured in other ways than those specifically described.

Figure 1:
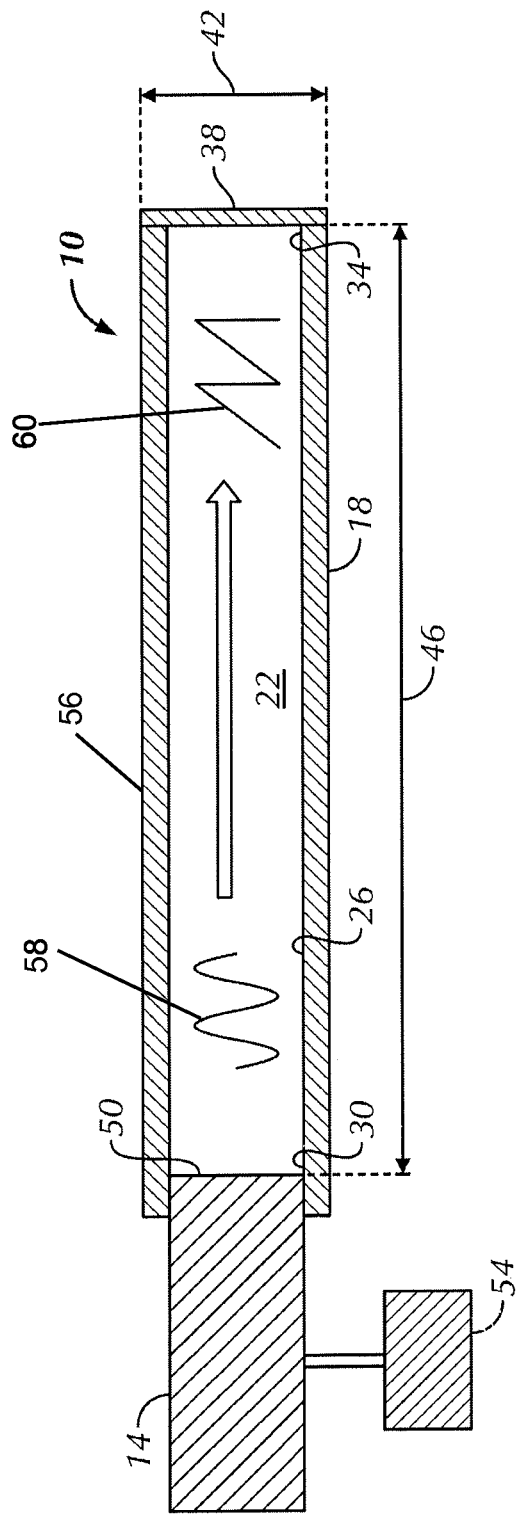
FIG. 1 depicts one embodiments of the present apparatuses for generating therapeutic shock waves.

Referring now to the drawings, and more particularly to FIG. 1, shown therein and designated by the reference numeral 10 is one embodiment of the present apparatuses for generating shock waves in a controlled manner. Certain embodiments of the apparatus of the present disclosure generate high frequency shock waves in a predictable and consistent manner. In one embodiment, the generated shock waves comprise that can be used in for medical and/or aesthetic therapeutic applications. Preferably, the generated high frequency shock waves are delivered to tissue of a patient. The shock waves can be configured to impose sufficient mechanical stress to the targeted cells of the tissue to rupture the targeted cells. In one embodiment, the rupture of the targeted cells occur at least through membrane-degradation damage. When targeted cells are exposed to the generated high-frequency shockwaves, they experience sharp gradients of mechanical stress due to the spatial heterogeneity parameters of the cells, such as density and shear elasticity modulus of the different components of the cell. For instance, dense and/or inelastic components inside a cell undergo greater mechanical stress when subjected to shock waves as compared to lighter components. In particular, acceleration of higher-density particles or components within the cellular structure exposed to the impact front is typically very large. At the same time, the impact on lower-density biological structures making up the cell structure when exposed to such a large gradient of pressure is significantly reduced because the elasticity of the lower-density biological structures allow them to generally act as low-compliance material. The difference in mechanical stress results in movement of the dense and/or inelastic components within the cell. When the cell is exposed to repeated shock waves at a certain frequency and energy level, the dense and/or inelastic components are repeatedly moved until they break out of the cell, thereby rupturing the cell. In particular, the properties mismatch of the cellular structure and cells' ability to experience deformation when exposed to the impact front lead to cellular destruction as described. Not intending to be bound by theory, one possible theory to explain the phenomenon of rupturing cellular structure can be found in Burov, V. A., Nonlinear ultrasound: breakdown of microscopic biological structures and non-thermal impact on malignant tumor. *Doklady Biochemistry and Biophysics Vol.* 383, pp. 101-104 (2002) (hereinafter "Burov"), which is incorporated herein by reference in its entirety.

While a cell may oscillate as an integral unit when impacted by these pressure fronts, sharp gradients of mechanical stress can be generated inside the cell as a result of spatial heterogeneity parameters (i.e., density and shear elasticity modulus). This concept can be illustrated by modeling the biological structure as two linked balls with masses $m_1$ and $m_2$ and the density $(\rho_0)$ of the liquid oscillating around the balls with the speed $\mu_o(t)$ differ insignificantly from the densities of the balls (by $\rho_1$ and $\rho_2$ respectively). If only the resistance to potential flow is taken into account, the force applied to the link is calculated as shown in Equation (1):

$$F = \frac{2}{3} \frac{m_1 m_2}{m_1 + m_2} \frac{[\rho_1 - \rho_2]}{\rho_0} \mu_0(t) \quad (1)$$

Additional discussions of Equation (1) and its variables are further provided in Burov. For example, if the ball radius (R) is about 10 μm and the difference between the densities of the balls is $0.1\rho_0$, and results in a stress force, $F/(\pi R^2)$m of $10^9$ dyne/cm$^2$. This is sufficient to rupture a cell membrane. The embodiments of the present apparatuses generate shock waves in a controlled manner that can be used to cause targeted damage to certain cells, which have medical and/or aesthetic therapeutic applications that are discussed further below.

Another possible theory to explain the phenomenon of cell rupturing is the accumulation shear stress in the denser material in the cellular structure. In heterogeneous media, such as cells with particles (e.g., pigment particles), shock waves cause the cell membranes to fail by a progressive (i.e., accumulated) shearing mechanism. On the other hand, in homogeneous media, compression by shock waves causes minimal, if any, damage to membranes. Microscopic focusing and defocusing of the shock wave as it passes through the heterogeneous media can result in shock wave strengthening or weakening locally that results in an increase in local shearing. Relative shearing motion of the cell membrane occurs on the scale of the heterogeneities of the cellular structure. It is believed that when shock waves strike a region of heterogeneities (e.g., cells containing particles), the particle motion that is out of phase with the incoming waves generates cell disruptive energy transfer (e.g., shear stress). The out of phase motion (e.g., shear stress) causes microscopic damage to the cell membrane that can progressively grow into cell membrane failure with additional successive accumulation of shear stress. The progressive shearing mechanism of repeated exposure to shock waves can be considered dynamic fatigue of the cell membranes. Damage from dynamic fatigue is dependent on three factors: (1) applied stress or strain, (2) the rate at which the strain is applied, and (3) accumulated number of strain cycles. These three factors can be manipulated to cause a cell with heterogeneities to experience catastrophic cell membrane failure as compared to a relatively more homogeneities at a particular applied strain, strain rate, and strain cycles. The manipulation of the factors can be done by providing shock waves of certain properties, such as the number of shock waves, the amount of time between each shock wave, and the strength of the applied shock waves. For instance, if there is too much time between shock waves for the tissue to relax to its unstrained state, the cells will become more resistant to failure. As such, in the preferred embodiment, high frequency shock waves (at least about 1,000,000 shock waves per second from acoustic waves with frequency of about 1 MHz) are delivered to the targeted cellular structures to achieve dynamic fatigue of the tissue and not allow the tissue time to relax.

A third possible theory is that the shock waves cause a combination of effects of direct movement of the particles contained in the cellular structure and dynamic fatigue that rupture the cells. While particle-containing cells are an apparent example of cellular structures exhibiting heterogeneities, their description are not intended to limit the scope of the present disclosure. Instead, the embodiments disclosed herein can be used to rupture or cause damage to other cellular structures that exhibit heterogeneities, such as cellular structures that have different effective density regions. The parameters of the shock waves generated according to the disclosed aspects can be adjusted based, at least on, the regions of different effective densities (i.e. heterogeneities) to cause cellular damage as described herein. Heterogeneities can be regions within a single cell, a region of different types of cells, or a combination of both. In certain embodiments, a region of heterogeneity within a cell includes a region having an effective density greater than the effective density of the cell. In one specific example, the effective density of a fibroblast cell is about 1.09 g/cm³, a region of heterogeneity in the cell would be particles contained within the cell that have an effective density greater than 1.09 g/cm², such as graphite with a density of 2.25 g/cm³. In certain embodiments, a region of cellular heterogeneity between cells includes a region with different types of cells, where each cell type has a different effective density, such as fibroblast cells and fat cells or hair follicles. The present disclosure provides further examples of cellular structures containing heterogeneities below.

Referring to FIG. 1, apparatus 10 comprises: an acoustic-wave generator 14, a shockwave housing 18 coupled to acoustic-wave generator 14, and a shockwave medium 22 disposed in shockwave housing 18. In the preferred embodiment, shockwave housing 18 defines chamber 26. Shockwave housing 18 can comprise, for example, polymer, plastic, silicone, metal, and/or any other suitable material. Chamber 26 comprises input end 30 coupled to acoustic-wave generator 14, output end 34, and body 56 extending between input end 30 and output end 34. In one embodiment, shockwave housing 18 further includes end cap 38 covering output end 34 of chamber 26. Referring to FIG. 1, chamber 26 has a circular cross-sectional shape. In other embodiments, chamber 26 has a rectangular, square, ovular, triangular, octagonal, and/or any other suitable cross-sectional shape. In the preferred embodiment, apparatus 10 further comprises shockwave medium 22 disposed in chamber 26 between input end 30 and output end 34.

In the preferred embodiment, acoustic-wave generator 14 is configured to emit a series or plurality of acoustic waves 58 from output 50, at least a portion of which enters chamber 26 and travels through shockwave medium 22 toward output end 34. As the acoustic waves move through shockwave medium 22, the properties of shockwave medium 22 alter acoustic waves 58 to form shock waves 60 at or near output end 34.

In the preferred embodiment, acoustic-wave generator 14 is configured to emit shock waves having at least one frequency between about 1 megahertz (MHz) and about 1000 MHz (e.g., 1 MHz, 2 MHz, etc.). In addition to or alternatively, acoustic-wave generator 14 is configured to emit at least one wavelength corresponding to at least one frequency between 1 MHz and 1000 MHz in the shockwave medium 22, or in a reference medium such as, for example, atmospheric air. In one embodiment, acoustic-wave generator 14 comprises an ultrasound head (e.g., a commercially available ultrasound head). In other embodiments, acoustic-wave generator 14 comprises ceramic and/or a piezoelectric acoustic element. In some embodiments, acoustic-wave generator 14 is configured to emit acoustic waves with beam radian power of between about, or substantially equal to 5 and about 1000 Watts per square centimeter (W/cm²) (e.g., 5 to 50 W/cm², 5 to 100 W/cm², 100 to 500 W/cm², 100 to 400 W/cm²).

Progressive nonlinear distortion of the waveform can result in the formation of pressure impact fronts, or shock waves. To form shock waves 60 at or near output end 34, shockwave medium 22 preferably comprises a material that exhibits or is able to allow acoustic waves 58 generated or emitted from acoustic-wave generator 14 to experience nonlinearities when the acoustic waves propagate through the material. The nonlinearities are preferably sufficient to transform the sinusoidal acoustic waves propagating therethrough into sawtooth-shaped waves with one shock per cycle, as illustrated by FIG. 1. In particular, progressive nonlinear distortion of the sinusoidal wavelength can result in formation of impact fronts that periodically follow each other with the frequency f. The duration of the front may be much shorter than the period 1/f as shown in Equation (2):

$$t = \frac{b}{\epsilon}(2I\rho c)^{1/2} \tag{2}$$

where b is the effective viscosity; $\epsilon$ is the nonlinear factor; and $\rho$ and c are the medium density and speed of sound, respectively. Additional discussions of Equation (2) and its variables are further provided in Burov. Because of the relatively high frequency of the acoustic waves, the shock waves are also generated at high frequency, at one shock wave per cycle. For example, certain embodiments of the present disclosure can be configured to generate about 1,000,000 shock waves per second from an acoustic wave of about 1 MHz. In other embodiments, apparatus 10 is configured to generate 100 or more shockwaves per minute (e.g., 200, 300, 400, 500, 1000, 2000, 5000, or more shock waves per minute).

Some embodiment of the present methods of generating therapeutic shock waves, comprise: actuating an acoustic-wave generator (e.g., 14) to emit acoustic waves having at least one frequency between 1 MHz and 1000 MHz, such that at least some portion of the acoustic waves travel through a shockwave medium (e.g., 22) that is disposed in a shockwave housing (e.g., 18) to form one or more shock waves. For example, in embodiments of the present methods may comprise actuating an acoustic-wave generator of any of the present apparatuses.

The nonlinearities distortion of acoustic waves 58 can be induced from the diffraction of the ultrasound waves from the wall of shockwave housing 18. Additionally or alternatively, nonlinearities may result from heterogeneities induced by ultrasound waves traveling through shockwave medium (or media) 22. Furthermore, nonlinearities can result from inclusion of particles or bubbles in the media (i.e. gas bubbles, nanoparticles, etc.). In some embodiments, shockwave medium 22 comprises a fluid. In some embodiments, shockwave medium 22 comprises a gel. In some embodiments, shockwave medium 22 comprises a liquid. In some embodiments, shockwave medium 22 is configured such that in the presence of acoustic waves from acoustic-wave generator 14, shockwave medium 22 will exhibit nonlinear properties. In some embodiments, shockwave medium 22 comprises one or more of: water, glycerin, poly(ethylene glycol) (PEG), propylene glycol, silicone oil, alcohol, or a combination of two or more of these. In some embodiments, shockwave medium 22 comprises one or more of: bubbles (e.g., gas bubbles), solid particles, or a combination of bubbles and solid particles. Gas bubbles can be introduced into medium 22, for example, by the addition of a gas such as carbon dioxide, and/or can be introduced in the form of stabilized gas bubbles found in ultrasound contrast media or as part of nanoparticles.

In addition, there are two other factors that affect the transformation of acoustic waves propagating through shockwave medium 22 into shock waves: shockwave formation length and absorption length of shockwave medium 22. Length of the nonlinearities distortion is a factor because the distortion is progressive and needs to sufficiently promulgate for the transformation to take place.

In some embodiments, the length of shockwave medium 22 or shockwave formation distance is a function of a nonlinear parameter, pressure amplitude, frequency of the acoustic wave generated by acoustic generator 14, the density of shockwave medium 22, and the speed of sound in shockwave medium 22. For example, the distance between when acoustic waves leaving acoustic-wave generator 14 and enters shockwave medium 22 and when the acoustic waves exit shockwave medium 22 is preferably greater than or equal to that given by Equation (3):

$$L = \frac{c_0^3 \rho_0}{\epsilon \omega P_0} = \frac{\lambda}{2\pi M_\omega} \quad (3)$$

where $\epsilon$=nonlinear parameter of shockwave medium; $\omega$=frequency of acoustic wave; $\rho_0$=density of the shockwave medium; $\lambda$=wavelength of acoustic wave; $c_0$=velocity of sound in the shockwave medium; $P_0$=pressure amplitude in shockwave medium; and $M_\omega$=acoustic mach number=$P_0 \div (c_0^2 \rho_0)$. In general, the higher the frequency and/or the higher the intensity of the acoustic waves, the shorter the minimum length of shockwave medium 22 needs to be to permit shock wave formation when the wave energy exits shockwave medium 22. Referring to FIG. 1, in the preferred embodiment, the length of shockwave medium 22 is represented by numeral 40, which runs from output 50 of acoustic wave generator 14 to output end 38 of shockwave chamber 26.

In the preferred embodiment, shockwave medium 22 has at least the minimum length to transform acoustic waves into shock waves for emitted acoustic waves with amplitude and frequency in a particular range, preferably the desired range of operation of at least 1 MHz. The minimum length is preferably determined by Equation 3 above. In some embodiments, shockwave medium 22 has a length that is greater than the minimum length determined to ensure shock waves are generated within shockwave medium 22 before the energy exit shockwave medium 22. In one embodiment, housing 18 is configured to have substantially the same length as shockwave medium 22 so the generated shock waves are promptly delivered from output end 34 to the treatment surface. In other embodiments, housing 18 can provide a gap between the end of shockwave medium 22 and output end 34. With the length of shockwave medium 22 configured to generate shock waves from acoustic waves of a certain amplitude and frequency, that length is also sufficient to convert any acoustic waves of greater amplitude and frequency than the designed range into shock waves.

In addition to shockwave formation length (for instance, length of shockwave media 22), the absorption length of shockwave medium 22 is another factor because absorption of acoustic energy prevents the formation of shock waves or can lead to the elimination of any formed shock waves. Absorption is based at least on the attenuation coefficient of the material of shockwave medium 22. Attenuation, in turn, is dependent on the frequency of the acoustic waves, which is preferably at least about 1 MHz as described above. Absorption is the inverse of the attenuation coefficient ($\alpha$) of shockwave medium 22, or 1/attenuation coefficient ($\alpha$).

In the preferred embodiment, the material of shockwave medium 22 is selected based on the relationship between shockwave formation length and absorption. In one embodiment, the relationship is represented by the Goldberg (r) number shown in Equation (4):

$$r = I_s/I_a \quad (4)$$

where: $I_s$=shockwave formation distance=(c03 p0)/($\epsilon\omega$P0) described in Equation (3) and $I_a$=absorption length=inverse of the attenuation coefficient=1/$\alpha$ Further discussions of the Goldberg number can be found in Brooks L A, Zander A C, Hansen C H, Investigation into the feasibility of using a parametric array control source in an active noise control system, Proceedings of ACOUSTICS 2005, 9-11, the disclosure of which is incorporated by reference in its entirety. Preferably, shockwave medium 22 comprises materials that have a positive Goldberg number at frequencies of at least about 1 MHz and pressures at output 50 of acoustic wave generator 14 of at least about 1 MPa. More preferably, shockwave medium 22 comprises a material or combination of materials that have a Goldberg number of at least 1 or greater than 1. Further, shockwave medium 22 preferably comprises solid polymers with a solid. Examples of solid polymers with a Goldberg number of greater than 1 at frequencies greater than 1 MHz and pressures greater than 1 MPa include, but are not limited to, aqualene, Pebax (polyether block amides), water, gelatin, polyurethane elastomer, such as Pellethane 2363-80.

Accordingly, the present disclosure allows for controlled generation of shock waves from acoustic waves by subjecting acoustic waves to sufficient progressive distortion nonlinearities to transform the sinusoidal waves into shock waves. This can be achieved by selecting the desired frequency and amplitude range, the absorption properties of the material, the length of the material based on the relationships described above. Because the factors affect one another, they can be adjusted to achieve the desired dimensions. For instance, if there is a desired length of shockwave medium 22, the frequency and amplitude of the emitted acoustic waves and the material of shockwave medium 22 to achieve this desired length. Other factors can be configured accordingly to achieve the desired result of generating shock waves from acoustic waves.

Referring to FIG. 1, acoustic wave generator 16 is coupled to housing 18, chamber 26, and shockwave media 22 to allow for propagation of at least a portion of the emitted acoustic waves 58 through shockwave media 22 to form shock waves 60. In some embodiments, input end 30 of chamber 26 has a transverse internal dimension (e.g., diameter 42) at least as large as a corresponding transverse external dimension of acoustic-wave generator 14 (e.g., at output 50). For example, in the embodiment shown, diameter 42 of chamber 26 is at least as large as (e.g., just larger than) the outer diameter of a corresponding portion (e.g., output 50) of acoustic-wave generator 14. In other embodiments, diameter 42 can be larger (e.g., and/or a gasket or coupler can be used to couple housing 18 to output end 50 of acoustic-wave generator). In the embodiment shown, chamber 26 has a substantially constant cross-section between input end 30 and outlet end 34. In other embodiments, chamber 26 has a varying cross-section between input end 30 and outlet end 34.

In some embodiments shockwave medium 22 and housing 18 comprise the same material, such as, for example, polymer, silicon, or any other suitable material (e.g., medium 22 may be unitary with housing 18 and/or end cap 38). In other embodiments, shockwave medium 22 is unitary with shockwave housing 18 (e.g. comprise the same piece of material). For instance, shockwave medium 22 comprises a solid material where a separate housing 18 is not necessary. In some embodiments, shockwave housing 18 and shockwave medium 22 comprise silicone. In other embodiments, shockwave medium 22 comprises one or more bubbles (e.g., gas bubbles or the like).

In some embodiments, shockwave housing 18 is configured such that distance 42 from acoustic-wave generator 14 (e.g., at input end 30 of chamber 26) to outlet end 38 of chamber 26 is between 100 and 1000 percent of at least one (e.g., the minimum) internal transverse dimension (e.g., diameter 42) of chamber 26. In some embodiments, distance 46 from acoustic-wave generator 14 (e.g., at input end 30 of chamber 26) to outlet end 34 of chamber 26 is between 300 and 900 percent (and/or between 400 and 800 percent) of at least one (e.g., the minimum) internal transverse dimension (e.g., diameter 42) of the chamber.

Additionally, in the embodiment shown, shockwave housing 18 is configured such that if acoustic waves 58 are incident on shockwave housing 18 from within shockwave chamber 26, then shockwave housing 18 will reflect at least some portion of the incident acoustic waves back into shockwave chamber 26.

Referring to FIG. 1, end cap 38 is configured enclose outlet end 34 of chamber 26 such that shockwave medium 22 is substantially prevented from exiting chamber 26, and to permit shock waves to exit output end 34 of shockwave chamber 26. In some embodiments, end cap 38 is configured to have a low shockwave attenuation (e.g., such that attenuation of a shockwave exiting end cap 38 will be less than twenty percent) and/or low shockwave reflection. In some embodiments, end cap 38 comprises at least one of: polymer, hydrogel, membrane, plastic, or silicone.

Referring to FIG. 1, apparatus 10 further comprises: controller 54 coupled to acoustic-wave generator 14 and configured to actuate acoustic-wave generator 14 to emit acoustic waves. Controller 54 can comprise any suitably programmed hardware, such as, for example, a processor with memory, a programmable logic controller (PLC), and a personal digital assistant (PDA), and/or the like. Although illustrated as a separate component, controller 54 can be integrated into (e.g., share a common housing with) acoustic-wave generator 14. In some embodiments, controller 54 is configured to adjust acoustic-wave generator 14 to vary at least one of the amplitude and frequency of acoustic waves emitted from acoustic-wave generator 14. In some embodiments, controller 54 is configured to actuate acoustic-wave generator 14 to continuously emit acoustic waves for a period of time (e.g., when acoustic-wave generator is actuated to be 'on'). In some embodiments, controller 54 is configured to actuate acoustic-wave generator 14 to emit acoustic waves 58 in a periodic on-off sequence (e.g., a sequence with regular, periodic intervals). In some embodiments, controller 54 is configured to actuate acoustic-wave generator 14 to emit acoustic waves 58 in an intermittent on-off sequence (e.g., a non-periodic sequence without regular, periodic intervals). Actuation of acoustic-wave generator 14 in an on-off sequence can, for example, reduce heat buildup in tissue. In some embodiments, controller 54 is configured to actuate acoustic-wave generator 14 to emit acoustic waves 58 in an on-off sequence, and to adjust the duration of "on" and/or "off" portions of the on-off sequence based on or responsive to measured and/or predicted temperature. For example, temperature can be measured with a thermometer (e.g., infrared thermometer) coupled to controller 54, and/or controller 54 can be configured to predict tissue temperature based, at least in-part, on intensity and/or other properties of acoustic waves 58 emitted from acoustic-wave generator 14 and/or shock waves 60 generated in housing 18 or delivered to tissue.

In some embodiments, acoustic-wave generator 14 is a first acoustic-wave generator, and apparatus 10 further comprises: a second acoustic-wave generator (not shown) configured to emit acoustic waves having at least one frequency between 1 MHz and 1000 MHz; where shockwave housing 18 is also coupled to the second acoustic-wave generator. In such embodiments apparatus 10 is configured such that if the second acoustic-wave generator emits acoustic waves then at least some portion of the acoustic waves will travel through shockwave medium or media 22 and form one or more shock waves. Some of these embodiments further comprise a controller 54 coupled to the second acoustic-wave generator and configured to actuate second the acoustic-wave generator to emit acoustic waves. In some embodiments, controller 54 is configured to actuate first acoustic-wave generator 14 and the second acoustic-wave generator (not shown) such that the acoustic waves that are emitted from the second acoustic-wave generator are out-of-phase from the waves that are emitted from first acoustic-wave generator 14.

In some embodiments, apparatus 10 is configured to fit within a box having a length of 3 feet, a width of 2 feet, and a height of 2 feet. In some embodiments, apparatus 10 is configured to fit within a box having a length of 3 feet, a width of 1 foot, and a height of 1 foot. In some embodiments, apparatus 10 is configured to fit within a box having a length of 2 feet, a width of 1 foot, and a height of 1 foot. In some embodiments, apparatus 10 is configured to fit within a box having a length of 1 feet, a width of 8 inches, and a height of 8 inches. For example, in some embodiments, housing 18 has an internal length of less than 3 inches, and an internal maximum transverse dimension (e.g., diameter) of less than 3 inches. In some embodiments, the internal length (between output end 50 of acoustic-wave generator 14, and output end 34 and/or internal surface of end cap 38). In some embodiments, apparatus 10 can be configured to generate pressures at targeted cells of over 3 megapascals (MPa) (e.g., 10 MPa or more).

Figure 2:
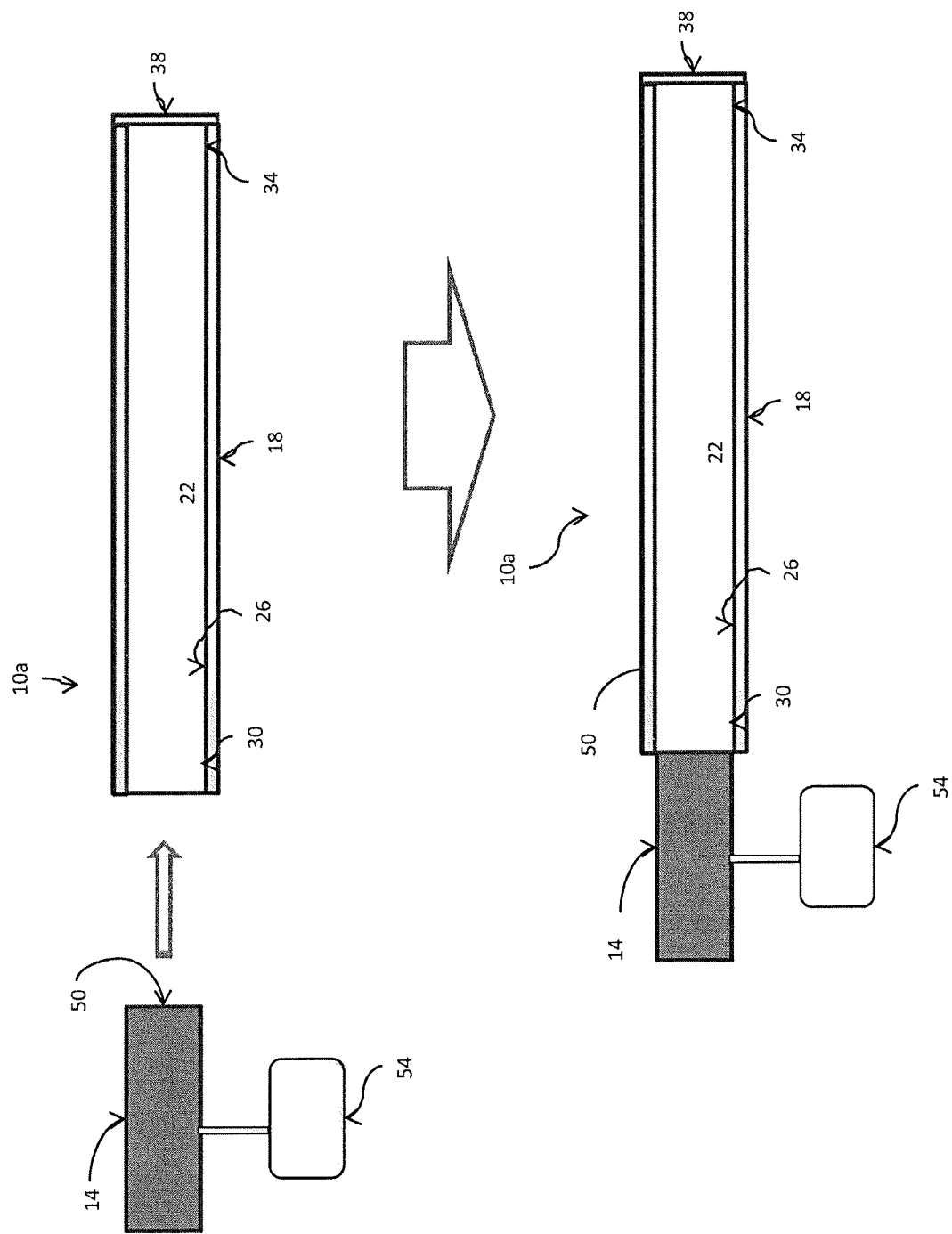
FIG. 2 depicts a second embodiment of the present apparatuses that comprises two complementary parts that can be removably coupled to one another, shown in disassembled and assembled configurations.

In the embodiment of FIG. 2, a second embodiment 10a of the present apparatuses is shown in disassembled and assembled configurations. Apparatus 10a is similar in many respects to apparatus 10, and may include any features of apparatus 10 not specifically excluded, such that the differences are primarily addressed here. In the embodiment shown, acoustic-wave generator 14 and shockwave housing 18 of apparatus 10a are configured to be removably coupled to one another such that the acoustic-wave generator can be actuated to emit acoustic waves that will travel through the shockwave medium and form one or more shock waves (e.g., as described for apparatus 10). In such embodiments, input end 30 may be sealed independently of acoustic wave generator 18 to prevent escape of medium 22 from housing 18 if acoustic-wave generator 14 is not coupled to housing 18. Acoustic-wave generator 14 and/or housing 18 can be configured in any suitable way to be removably coupled together (e.g., with threads, interlocking tabs, a press fit permitting the acoustic-wave generator to be inserted into input end 30 of the housing, etc.). In some embodiments, acoustic-wave generator 14 and housing 18 are not connected in such a way that separation is physically resisted. For example, in some embodiments, housing 18 is placed adjacent a patient with output end 34 pointing toward target cells, and acoustic-wave generator 14 is coupled to (e.g., positioned in contact with) housing 18 without inserting acoustic-wave generator 14 into housing 18 or otherwise physically interconnecting the two. In some embodiments, different housings 18 may be provided with different characteristics (e.g., dimensions, media 22, end caps 38, etc.), such that different housings 18 may be coupled to a single acoustic-wave generator 18 to produce shockwaves with different characteristics. In such embodiments, housing 18 may be a single-use device that is disposable and/or disposed of after each use.

While the high frequency shock waves generated by certain embodiments of the present disclosure and the controlled and predictable manner of generating them have many applications, certain embodiments of the present disclosure and the generated shock waves are particularly useful in therapeutic applications. Specifically, in treating certain skin conditions of a patient. As described above, high frequency shock waves can lead to controlled and targeted rupture of cellular structures based on the elasticity difference in the components of the cellular structures. The ability to provide targeted and controlled rupture or damage of certain cellular structures is particularly applicable to treating maladies and/or conditions that involve particles agglomerated in cells ("cellular particle agglomerates") that create a differential in elasticity of the cellular structure. In particular, certain embodiments of the present invention, e.g., apparatus 10, can consistently and/or predictably generate shock waves at high frequency to rupture particular cells in a targeted manner without inducing cavitation in a patient's tissue and without generating a high amount of thermal energy (e.g., heat) in the skin of the patient that could lead to further unintended damage. Released particles can be removed from the surrounding tissue through the normal absorptive processes of the patient.

Examples of maladies and/or conditions that involve particles agglomerated in cellular structures include cancer, crystalline micro-particles in the musculoskeletal system, or removal of tattoos. These are merely no limiting exemplary conditions that can be treated or addressed by rupturing or destruction of cells containing particle agglomerates. In some embodiments, destruction of the cells containing particle agglomeration may be caused by non-thermal cell membrane degradation of the specific cells secondary to nonlinear processes accompanying propagation of high frequency shock waves, as discussed above.

Tattoos are essentially fibroblast cells that contain agglomerates of ink particles. Because the captured ink particles are denser than the biological structures of the fibroblast cells, tattoos or fibroblast cells containing ink particles have a large difference in elasticity in its structure. When subject to shock waves, the fibroblast cells containing ink particles are subject to greater mechanical strain as compared to other fibroblast cells that do not contain dense particles. Shock waves can be configured to be delivered at an optimal frequency and amplitude to accelerate the ink particles sufficiently to rupture the particular fibroblast cells while leaving intact fibroblast cells that do not have the particular elasticity difference. The details of tattoos and biological process of removal of released from fibroblast cells are discussed further below.

A. Tattoos

Tattoo inks and dyes were historically derived from substances found in nature and generally include a heterogeneous suspension of pigmented particles and other impurities. One example is India ink, which includes a suspension of carbon particles in a liquid such as water. Tattoos are generally produced by applying tattoo ink into the dermis, where the ink generally remains substantially permanently. This technique introduces the pigment suspension through the skin by an alternating pressure-suction action caused by the elasticity of the skin in combination with the up-and-down movement of a tattoo needle. Water and other carriers for the pigment introduced into the skin diffuse through the tissues and are absorbed. For the most part, the insoluble pigment particles are deposited in the dermis where placed. In tattooed skin, pigment particles and agglomerates are generally found in the cytoplasm of the skin cells (e.g., dermal fibroblasts) (i.e., in the membrane-bound structures known as secondary lysosomes). This may be due to active phagocytosis into dermal cells (e.g., macrophages, fibroblasts). Resulting pigment agglomerates ("particle agglomerates") may range up to a few micrometers in diameter. Once the skin has healed, most pigment particles remain in the interstitial space of the skin tissue. Tattoo inks generally resist elimination due to their inertness and the relatively large size of insoluble pigment particles. A tattoo may fade over time, but will generally remain through the life of the tattooed person.

Tattoo inks typically comprise aluminum (87% of the pigments), oxygen (73% of the pigments), titanium (67% of the pigments), and carbon (67% of the pigments). The relative contributions of elements to the tattoo ink compositions were highly variable between different compounds. Additional information can be found in Timko, A L; Miller, C H; Johnson, F B; Ross E V: In Vitro Quantitative Chemical Analysis of Tattoo Pigments, *Arch Dermatol* Vol 137, February 2001, 143-147, the disclosure of which is incorporated by reference in its entirety. The diameters of the pigments may vary from about 20 nm to about 900 nm. Transmission electron microscopy (TEM) images of pigments showed a variety of shapes (e.g., needles, platelets, cubes, bars, and a number of irregular shapes). In addition to primary particles, aggregates composed of primary particles grown together at their surfaces and agglomerates (groups of single crystals joined together at their edges) were observed in the same TEM images. The full details of the TEM images are in Baumler, W; Eibler, E T; Hohenleutner, U; Sens, B; Sauer, J; and Landthaler, M; Q-switched laser and tattoo pigments: First results of the chemical and photophysical analysis of 41 compounds. *Lasers in Surgery and Medicine* 26:13-21 (2000), which is incorporated by reference in its entirety.

At least one study has determined the particle size for three commercial tattoo inks as shown in Table 1:

TABLE 1

Tattoo Pigment Particle Size

| Color | Mean Diameter | Std deviation |
| --- | --- | --- |
| Viper Red | 341 nm | 189 nm |
| Agent Orange | 228 nm | 108 nm |
| Hello yellow | 287 nm | 153 nm |

B. Tattoo Removal

In conventional tattooing (decorative, cosmetic, and reconstructive), once the pigment or dye has been administered into the dermis to form a tattoo, the pigment or dye generally remains permanently in place. This generally may be attributed to active phagocytosis into dermal cells (macrophages, fibroblasts) that prevent the particles from being absorbed and dispersed into the body. The resulting pigment agglomerates ("particle agglomerates") can range up to a few micrometers in diameter.

Despite the general permanency of tattoos, individuals may wish to change will remove tattoos for a variety of reasons. For example, over time people may have a change of heart (or mind), and may desire to remove or change the design of a decorative tattoo. By way of another example, an individual with cosmetic tattooing, such as eyeliners, eyebrows, or lip coloring, may wish to change the color or area tattooed as fashion changes. Unfortunately, there is currently no simple and successful way to remove tattoos. One approach that has been disclosed (see U.S. Patent Application Pub. No. US2003/0167964) is the use of tattoo inks that are removable on demand. Such inks may consist of microparticles that are constructed with specific electromagnetic absorption and/or structural properties that facilitate changing and/or removal by applying specific energy (such as electromagnetic radiation from a laser or flash-lamp). In other embodiments, pigments and/or pigment carriers may be susceptible to a specific externally applied energy source, such as thermal or light (e.g., laser light, infrared light, or ultraviolet light). One problem with this type of approach is that it requires these new types of ink, and has little or no effect on tattoos utilizing traditional pigments.

Currently, methods of removing traditional tattoos (e.g., pigment-containing skin) may include salabrasion, cryosurgery, surgical excision, and CO2-laser. These methods may require invasive procedures associated with potential complications, such as infections, and usually results in conspicuous scarring. More recently, the use of Q-switched lasers has gained wide acceptance for the removal of tattoos. Additional information about the use of Q-switched lasers for removing tattoo can be found in Ross, E V; Naseef, G; Lin, C; Kelly, M; Michaud, N; Flotte, T J; Raythen, J; Anderson, R R; Comparison of Responses of Tattoos to Picosecond and Nanosecond Q-Switched Neodymium:YAG Lasers. *Arch Dermatol* 134: 167-171 (1998), the disclosure of which is incorporated by reference in its entirety. By restricting pulse duration, ink particles generally reach very high temperatures with relatively minimal damage to adjacent normal skin. This significantly decreases the scarring that often results after nonselective tattoo removal methods, such as dermabrasion or treatment with carbon dioxide laser. The mechanisms of tattoo removal by Q-switch laser radiation this may still be poorly understood. It is thought that Q-switch laser allow for more specific removal of tattoos by the mechanisms of selective photothermolysis and thermokinetic selectivity. Further detail can be found in Solis, R R; Dayna, D G; Colome-Grimmer M O; Snyder, M; Wagner R F: Experimental nonsurgical tattoo removal in a guinea pig model with topical imiquimod and tretinoin, *Dermatol Surg* 2002; 28:83-877, which is incorporated by reference in its entirety. Specifically, it is thought that the pigment particles are able to absorb the laser light causing heating of the particles resulting thermal destruction of cells containing said particles. The destruction of these cells results in the release of particles which can then be removed from the tissue through normal absorptive processes.

While the Q-switch laser may be better than some alternatives for the removal of tattoos, it is not perfect. Some tattoos are resistant to all laser therapies despite the predicted high particle temperatures achieved through selective photothermolysis. Reasons cited for failure of some tattoos to clear include the absorption spectrum of the pigment, the depth of pigment, and structural properties of some inks Adverse effects following laser tattoo treatment with the Q-switched ruby laser may include textural changes, scarring, and/or pigmentary alteration. Transient hypopigmentation and textural changes have been reported in up to 50 and 12%, respectively, of patients treated with the Q-switched alexandrite laser. Hyperpigmentation and textural changes are infrequent adverse effects of the Q-switched Nd:YAG laser and the incidence of hypopigmentary changes are generally lower than with the ruby laser. The development of localized and generalized allergic reactions is also impossible (even if unusual) complication of tattoo removal with the Q-switched ruby and Nd:YAG lasers. Additionally, laser treatment may be painful, such that use of a local injection with lidocaine or topical anesthesia cream typically is used prior to laser treatment. Additional information on the effects of laser treatment can be found in Kuperman-Beade, M; Levine, V J; Ashinoff, R; Laser removal of tattoos. *Am J Clin Dermatol.* 2001; 2 (1):21-5, the disclosure of which is incorporated by reference in its entirety.

Finally, laser removal generally requires multiple treatment sessions (e.g., 5 to 20) and may require expensive equipment for maximal elimination. Typically, since many wavelengths are needed to treat multicolored tattoos, not one laser system can be used alone to remove all the available inks and combination of inks. Even with multiple treatments, laser therapy may only be able to eliminate 50-70% of the tattoo pigment, resulting in a residual smudge.

Some embodiments of the present methods comprise: directing shock waves (e.g., from an embodiment of the present apparatuses) to cells of a patient; where the shock waves are configured to cause particles to rupture one or more of the cells. Some embodiments comprise: providing an embodiment of the present apparatuses; actuating apparatus to former shockwaves configured to cause particles within a patient to rupture one or more cells of the patient; and directing the shockwaves to cells of a patient such that the shockwaves cause particles to rupture one or more of the cells (e.g., such as by degradation of the cell wall or membrane). In some embodiments, the one or more shockwaves are configured to have substantially no lasting effect on cells in the absence of particles (e.g., configured to cause substantially no permanent or lasting damage to cells that are not close enough to particles to be damaged by the particles in the presence of the shockwaves).

Some embodiments of the present methods comprise focusing the one or more shockwaves a specific region of tissue that comprises the cells. In some embodiments the region of tissue at which the one or more shockwaves is focused is a depth beneath the patient's skin. The shockwaves can be focused by any of a variety of mechanisms. For example, where the acoustic wave generator comprises an ultrasound head, the ultrasound head may be a parabolic ultrasound head such that the acoustic waves generated are focused by the parabolic shape in the targeted direction. By way of another example, in embodiments of the present apparatuses to comprise multiple acoustic-wave generators, the shockwaves can be focused by generating acoustic waves of different frequencies such that the acoustic waves and the resulting shockwaves are focused were directed by the interaction of the frequencies (e.g. in similar fashion to that of a phase- or array radar). Focusing the shockwaves may result in higher pressures at targeted cells, such as, for example, pressures of 10 MPa, 15-25 MPa, or greater.

Some embodiments of the present methods further comprise: identifying target cells of the patient to be ruptured (e.g., prior to directing the one or more shockwaves to the target cells). In various embodiments, the target cells can comprise any of a variety of target cells, such as, for example, target cells comprising a condition or malady involving cellular particle agglomerates. For example, the target cells may comprise: a tattoo, musculoskeletal cells comprising crystalline micro-particles, hair follicles that contain keratin protein, dental follicles that contain enamel, cancer cells, and/or the like. By way of another example, target cells may comprise one or more skin maladies selected from the group consisting of: blackheads, cysts, pustules, papules, and whiteheads.

In some embodiments, the particles can comprise non-natural particles. One example of non-natural particles includes tattoo pigment particles, such as are commonly disposed in the human dermis to create a tattoo. In some embodiments, the pigments can comprise an element with anatomic number of less than 82. In some embodiments, the particles can comprise any one or combination of: gold, titanium dioxide, iron oxide, carbon, and/or gold. In some embodiments, the particles have a mean diameter of less than 1000 nm (e.g., less than 500 nm and/or less than 100 nm).

Figure 3:
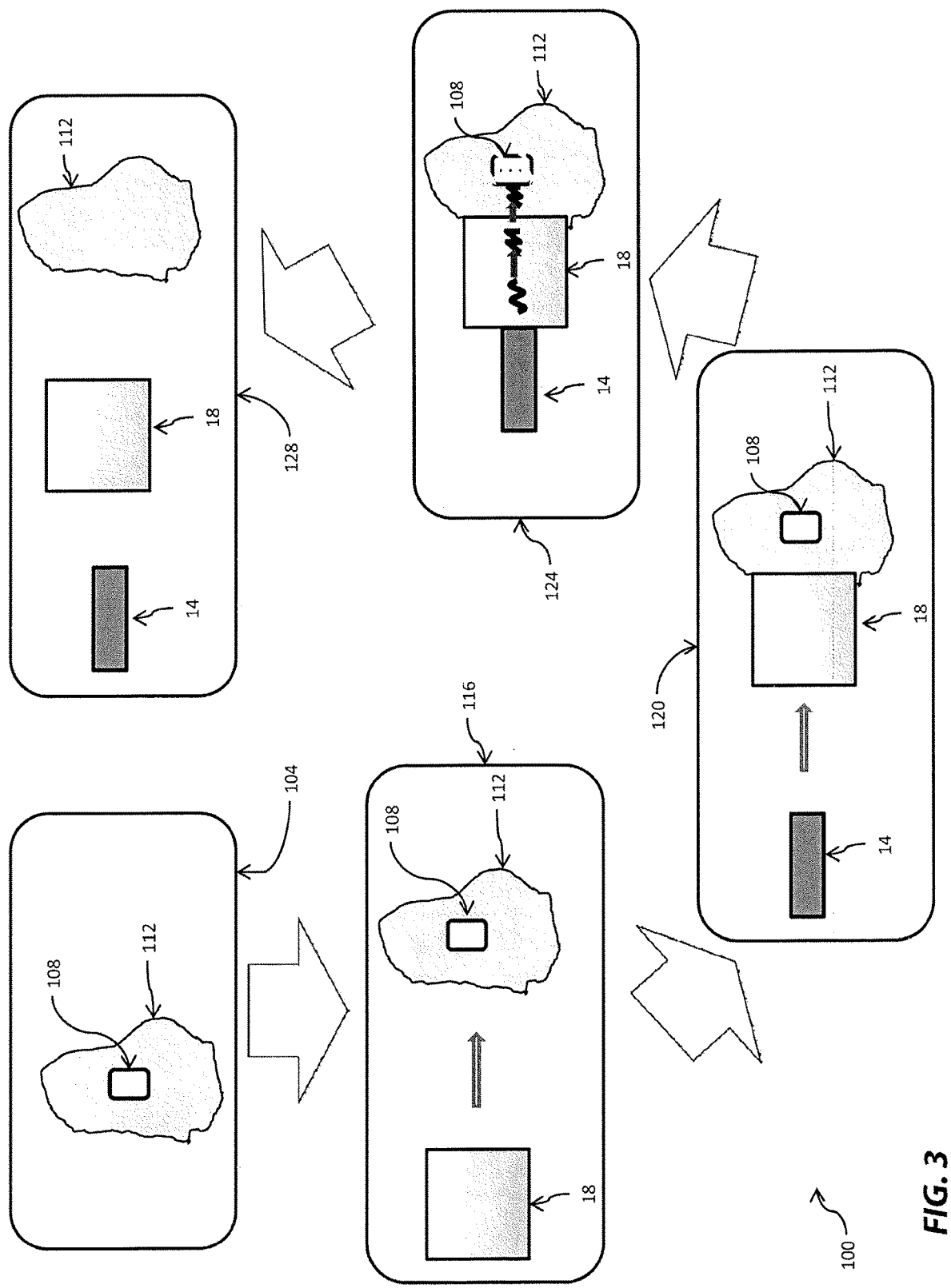
FIG. 3 depicts a conceptual flowchart of one of the present methods.

FIG. 3 illustrates one embodiment of a method 100 of using apparatus 10a to direct shockwaves to target tissue. In the embodiment shown, method 100 comprises a step 104 in which target cells 108 of a patient's tissue 112 are identified for treatment. For example, tissue 112 can comprise skin tissue, and/or target cells 108 can comprise fat cells within or near skin tissue. In the embodiment shown, method 100 also comprises a step 116 in which a housing 18 is disposed adjacent tissue 112 and/or tissue 116, such that shockwaves can be directed toward the target cells 108. In the embodiment shown, method 100 also comprises a step 120 in which acoustic-wave generator 14 is positioned adjacent (and/or coupled to) housing 18. In the embodiment shown, method 100 also comprises a step 124 in which acoustic wave generator 14 is activated to generate acoustic waves (while the acoustic wave generator and the housing are acoustically coupled) to form shockwaves in housing 18 for delivery to target cells 108, as shown. In the embodiment shown, method 100 also comprises a step 128 in which acoustic-wave generator 14 is de-coupled from housing 18, and housing 18 is removed from or moved relative to tissue 112. In the embodiment shown, target cells 108 are omitted from step 128, representing their destruction. Other embodiments of the present methods may comprise some or all of the steps illustrated in FIG. 3. Apparatus 10 can be implemented similarly to apparatus 10a, with the exception that apparatus 10 may not be configured to be disassembled, and thus, may be disposed to direct shockwaves to target cells as a single piece.

Methods of Removing Tissue Markings

In some embodiments of the present methods of diminishing tissue markings (e.g., tattoos) caused by pigments in dermis tissue involve the use of one of the present apparatuses. In such methods, high-frequency shockwaves are transmitted to and into a patient's skin, such that when the shock waves generated from the apparatus of the present disclosure reach the dermal cells and vibrate or accelerate the intradermal particles, these particles experience movement relative cell membranes that can lead to fatigue degradation and rupturing of cells, thereby releasing the pigment particles. Released particles can then be removed from the surrounding tissue through normal absorptive processes of the patient's body. In some embodiments, one of the present apparatuses can be disposed adjacent to, and/or such that the shock waves from the apparatus are directed to the tissue site having the tattoo, other tissue markings, or other cellular structures containing particle agglomerates. To cause particle alteration (e.g., cell degradation sufficient to release particles for absorption), the shock waves can be delivered to a specific area for a period of time long enough to rupture cells containing and/or adjacent to the pigment particles such that the pigment particles are released. In some embodiments the present apparatuses have a focus or effective area that may be relatively smaller than a tattoo, such that the apparatus may be periodically and are sequentially focused are directed at different areas of a tattoo to cause a reduction in perceptible pigments over the entire area of the tattoo. For instance, the parameters of the embodiments of the apparatus disclosed here can be modified to achieve the desire number of shocks delivered to a particular site in a desired amount of time. For instance, in one embodiment, shock waves are produced from acoustic waves with frequency of at least 1 MHz according to aspects of the present disclosure and exposed to a particular treatment site for the appropriate period of time to deliver at least about 100, 200, 300, 400, 500, or 1000 shock waves to the treatment site. The shock waves can be delivered all at once or through intervals (e.g., bursts) of shock waves (such as 5, 10, 15, 20, 25, 30, 40, 50, etc. shock waves at a time). The appropriate interval and time between the interval can be modified and/or determined to achieve the desired effect at the treatment site, e.g., rupture of the targeted cellular structures. It is understood that if acoustic waves with higher frequency are used, such as 2 MHz, 3 MHz, 4 MHz, or 5 MHz, the treatment time can be adjusted, likely shorter exposure time, to achieve the desired amount of shock waves delivered to the treatment area.

As will be appreciated by those of ordinary skill in the art, in embodiments of the present methods for removing tattoos, the particles affected by the shock waves comprise tattoo pigment (particles), such as may, for example, be at least partially disposed between and/or within skin cells of the patient. Such pigment particles may, for example, include at least one or combination of any of the following: titanium, aluminum, silica, copper, chromium, iron, carbon, or oxygen.

The use of high frequency shock waves to remove or reduce skin markings has many advantages over the use of lasers. For example, laser treatments for tattoo removal may be very painful. In contrast, high-frequency shockwaves (e.g., ultrasound shockwaves) can be configured and/or applied such that tattoos or other skin markings may be removed or diminished with little if any pain to the patient, especially, for example, where the shock waves are targeted or otherwise configured to degrade only cells that contain tattoo pigments. By way of another example, laser light directed at tissue has been found to cause damage to or destruction of surrounding tissues; whereas high-frequency shock waves may be applied so as to cause little damage or destruction of surrounding tissues (e.g., because non-tattooed surrounding tissues generally lack tattoo pigment or other particles that might otherwise interact with neighboring cells to cause sell degradation). Finally, laser tattoo removal often requires multiple treatment sessions (e.g., 5-20 sessions) for maximal tattoo elimination, and/or often requires the use of expensive equipment. Additionally, since many wavelengths a laser light may be needed to remove multicolored tattoos, multiple laser systems may be needed to remove the variety of available inks and/or combinations of available inks. As a result, the overall cost of laser tattoo removal may be prohibitively expensive. Even with multiple treatments, laser therapy may be limited to eliminating only 50 to 70% of tattoo pigment, and may leave a residual "smudge." In contrast, high-frequency shockwaves is not dependent upon the color of tattoo pigments such that therapeutic application of high-frequency shockwaves does not require different apparatuses for different colors of pigment, and such that high-frequency shockwaves may be applied to a relatively large area (e.g., the entire area of a tattoo), thereby reducing the number of treatment sessions required to achieve a level of tattoo removal or reduction that is acceptable to the patient (e.g., 30, 40, 50, 60, 70, 80, 90, 95, or more percent reduction in the perceivable pigment in the patient's skin).

In some embodiments, the present methods include the application of high-frequency shockwaves (e.g. with one or more of the present apparatuses) and the application of laser light. For example, some embodiments of the present methods further comprise directing a beam of light from a Q-switched laser at the target cells (e.g., tattooed skin). In some embodiments, directing one or more shockwaves and directing the beam of light are performed in alternating sequence.

In some embodiments, the present methods include delivering one or more chemical or biological agents (e.g., configured to aid in the removal of tissue markings such as tattoos) to a position at or near the target cells before, after, and/or simultaneously with directing the one or more shockwaves to the target cells. For example, some embodiments of the present methods further comprise applying a chemical or biological agent to the skin (e.g., before, after, and/or simultaneously with directing one or more shockwaves and/or a beam of laser light at the skin). Examples of chemical or biological agents include: chelators (e.g., ethylenediaminetetraacetic acid (EDTA)); immune modulators (e.g., Imiquimod [5]); combinations thereof; and/or other suitable chemical in or biological agents. In various embodiments, chemical in or biological agents to be delivered transdermally and/or systemically (e.g., the injection) to the target cells (e.g., may be applied topically to tattooed skin).

Some embodiments of the present methods of tattoo removal include multiple applications of shockwaves to tattooed skin tissue (e.g., for a duration of at least 1 second (e.g., 10 seconds, or more), once per week for 6 or more weeks).

Method of Treating Additional Maladies and Conditions

In addition to tattoo removal, embodiments of the present methods may include the application of high-frequency shockwaves to treat a variety of maladies under conditions caused by and/or including symptoms of cellular particle agglomerates and/or particles disposed in intracellular spaces and/or interstitial spaces. For example, such maladies and/or conditions may include: crystal joint, ligament, tendon and muscle disease, and/or dermatological maladies involving particle agglomerates including acne, age spots, etc. Additionally, embodiments of the present methods may include the application of high-frequency shockwaves after delivering nanoparticles to a region of the patient that includes the target cells. For example, in some embodiments, nanoparticles (e.g., gold nanoparticles) are delivered to a patient's bloodstream intravenously and permitted to travel to a region of the patient that includes the target cells (e.g. a cancerous tumor), such that high-frequency shockwaves can be directed to the target region to cause the nanoparticles to interact with and rupture the target cells.

Further, embodiments of the present apparatuses (e.g., apparatus 10) can be used for wrinkle reduction. For example, some embodiments of the present methods of generating therapeutic shock waves, comprise: providing any of the present apparatuses (e.g., apparatus 10); and actuating the apparatus to generate one or more shock waves. Some embodiments further comprise: disposing the apparatus (e.g., outlet end 34 of housing 18) adjacent tissue of a patient such that at least one shock wave enters the tissue. In some embodiments, the tissue comprises skin tissue on the face of the patient.

In embodiments of the present methods that include directing particles (e.g., micro-particles and/or nanoparticles) to a position at or near the target cells (prior to directing shockwaves to the cells), the particles can comprise: silk, silk fibron, carbon nanotubes, liposomes, and/or gold nanoshells. For example, in some embodiments, directing the particles can comprises injecting into the patient a fluid suspension that includes the particles. Include suspension may, for example, comprise saline and/or hyaluronic acid.

Deposition of crystals and other miscellaneous crystals in articular and particular tissues can result in a number of disease states. For example, monosodium urate monohydrate (MSUM) deposition in a joint may results in gout. As another example, calcium pyrophosphate dehydrate (CPPD) in joint tissues and fluids may result in a number of disease conditions, such as, for example, chondrocalcinosis (i.e., presence of calcium-containing crystals detected as radiodensities in articular cartilage). By way of further example, hydroxyapatite (HA) crystal deposition may result in calcific tendonitis and perarthritis. In some embodiments of the present methods, the particles may comprise natural particles (e.g., particles naturally occurring within the body), such as, for example, crystalline micro-particles such as may be form and/or become disposed in the musculoskeletal system of a patient. Other examples of natural particles they may be treated and/or disbursed in the present methods include: urate crystals, calcium-containing crystals, and/or hyroxyapatite crystals.

In embodiments of the present methods that for treatment of acne or other skin-based conditions, the particles may comprise dirt and/or debris that is disposed in one or more pores of the patient's skin, and/or may comprise keratin protein disposed of the patient's skin.

Some embodiments of the present methods of treating tumors or other maladies include multiple applications of shockwaves to targeted tissue (e.g., a tumor, an area of skin with acne or other conditions, etc.), such as, for example, for a duration of at least (e.g., 10 seconds, or more), once per week for 6 or more weeks.

The various illustrative embodiments of devices, systems, and methods described herein are not intended to be limited to the particular forms disclosed. Rather, they include all modifications and alternatives falling within the scope of the claims. For example, the present methods can include any combination of the steps and features described in the embodiments above (e.g., in combination with other steps or features) in any combination and/or repetition.

The claims are not intended to include, and should not be interpreted to include, means-plus- or step-plus-function limitations, unless such a limitation is explicitly recited in a given claim using the phrase(s) "means for" or "step for," respectively.

As disclosed, certain embodiments of the present invention provide advantages over other methods employing ultrasound in therapeutic applications. For instance, U.S. Pat. No. 5,618,275 discusses a method of facilitating the penetration of a therapeutic agent through a person's skin by applying relatively low frequency ultrasonic pressure waves in a range of about 15,000 to about 25,000 Hz to the skin of sufficiently high intensity to cause cavitation in the skin. The effect of the low frequency ultrasonic pressure waves is to increase the permeability of the skin to allow penetration of therapeutic agents for a limited time period. In another example, U.S. Pat. No. 6,487,447 discloses an apparatus that apply ultrasound radiation to a drug solution to be applied to a patient. The ultrasound radiation has a frequency in the range of 15 KHz and 1 MHz and is applied at intensity, for a period of time and at a distance from said skin area effective to generate cavitation bubbles. The cavitation bubbles collapse and transfer their energy into the skin area thus causing the formation of pores in the skin area. U.S. Patent Publication No. US2008/009774 (by the present inventor) discloses a method of treating maladies caused by particles in tissue through the use of ultrasound radiation. The ultrasound radiation has a frequency in the range of 15 KHz and 2 MHz and is applied at intensity and for a period of time effective to generate cavitation bubbles effective to collapse and transfer their energy into the particles resulting in the alteration of the particles. As mentioned above, the method of Klopotek U.S. Pat. No. 6,325,769) create a negative pressure, or vacuum effect, in the tissue in the wake of the pulse—which can induce tissue damage, tearing tissue structures apart, heating the region and, thereby, triggering the synthesis of new connected tissue. The disclosures of U.S. Pat. Nos. 6,325,769 and 6,487,447 and U.S. Patent Application Publication Nos. US2008/009774 and US2003/0167964 incorporated by reference in their entirety.

Unlike these methods, certain embodiments of the present disclosure achieves targeted destruction of cellular structures with heterogeneities (e.g., cells containing particles) with minimal cavitation destruction. Further, direct application of high ultrasonic energy of prior methods may result in the indiscriminant alteration, and potentially destruction, of cells other than those cells containing particle agglomerates. The generated shock waves of the present disclosure can be configured to rupture targeted cells without exposing non-targeted cells to thermal damage. That is, rupturing can be achieved with minimal indiscriminate heating of the surrounding area.

Although the embodiments of the present disclosure and their advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A method comprising:
providing a plurality of sinusoidal acoustic waves having at least one frequency between 1 MHz and 1,000 MHz;
propagating at least a portion of the sinusoidal acoustic waves through a shockwave medium disposed in and contained by a shockwave housing, the shockwave medium configured to exhibit nonlinear properties in the presence of the propagated sinusoidal acoustic waves to generate a plurality of unfocused shock waves that exit a distal end of the shockwave housing; and
delivering at least a portion of said plurality of unfocused shock waves to at least one cellular structure comprising at least one region of heterogeneity; and
rupturing the at least one cellular structure by continuing to deliver said plurality of unfocused shock waves;
wherein the plurality of unfocused shock waves are generated in the shockwave medium.

2. The method of claim 1 further comprising the step of varying the frequency of the sinusoidal acoustic waves or varying the amplitude of the sinusoidal acoustic waves.

3. The method of claim 1, wherein the at least one cellular structure is disposed outside of the shockwave housing and rupturing the at least one cellular structure is caused by non-thermal cell membrane degradation.

4. The method of claim 3, further comprising the step of directing laser light to the at least one cellular structure and wherein the delivering step comprises delivering at least a portion of said plurality of unfocused shock waves to an epidermis layer of a patient and wherein delivering the plurality of unfocused shock waves and directing the laser light are performed in an alternating sequence.

5. The method of claim 3, wherein rupturing the at least one cellular structure is performed via accumulation of shear stress in the at least one region of heterogeneity and without inducing cavitation.

6. The method of claim 1, wherein the plurality of shock waves are formed without focusing the acoustic waves, and wherein the housing is a handheld device.

7. The method of claim 1, further comprising the step of actuating a first ultrasound head to provide the plurality of sinusoidal acoustic waves.

8. The method of claim 1, further comprising:
identifying at least one target cellular structure to be ruptured prior to delivering at least a portion of the plurality of unfocused shock waves to the at least one target cellular structure.

9. An apparatus comprising:
an acoustic-wave generator configured to emit sinusoidal acoustic waves having at least one frequency between 1 MHz and 1000 MHz;
a shockwave medium contained by a shockwave housing wherein the shockwave housing is coupled to the acoustic-wave generator; and
wherein the apparatus is configured to propagate at least a portion of the emitted sinusoidal acoustic waves through the shockwave medium to form unfocused shock waves in the shockwave medium such that the unfocused shock waves exit a distal end of the shockwave housing; and
wherein the formed unfocused shock waves are configured to rupture to at least one cellular structure comprising at least one region of heterogeneity having a greater effective density than an effective density of another region of the at least one cellular structure.

10. The apparatus of claim 9, wherein the shockwave medium is configured to exhibit nonlinear properties in the presence of the sinusoidal acoustic waves emitted from the acoustic-wave generator.

11. The apparatus of claim 9, wherein the shockwave medium comprises one or more of: bubbles, solid particles, or a combination of bubbles and solid particles.

12. The apparatus of claim 9, wherein:
the apparatus is a hand-held apparatus;

the shockwave housing defines a chamber having an input end coupled to the acoustic-wave generator and an output end extending from the acoustic-wave generator; and the shockwave housing further comprises an end cap removably coupled to the output end of the chamber.

13. The apparatus of claim 12, wherein the end cap is configured to attenuate a shock wave exiting the end cap by less than twenty percent.

14. The apparatus of claim 9, wherein the length of the shockwave medium through which the emitted sinusoidal acoustic waves propagate is greater than or equal to L for at least one wavelength of the sinusoidal acoustic waves that the acoustic-wave generator is configured to emit, wherein L is determined by the following equation:

$$L = \frac{c_0^3 \rho_0}{\epsilon \omega P_0} = \frac{\lambda}{2\pi M_\omega}$$

where $\epsilon$=nonlinear parameter of shockwave medium; $\omega$=frequency of acoustic wave; $\rho_o$=density of the shockwave medium; $\lambda$=wavelength of acoustic wave; $c_0$=velocity of sound in the shockwave medium; $P_0$=pressure amplitude in shockwave medium; and $M_\omega$=acoustic mach number=$P_0 \div (c_0^2 \rho_o)$.

15. The apparatus of claim 14, wherein the shockwave medium has a Goldberg number of greater than or equal to 1, wherein the Goldberg number is determined by dividing the length of the shockwave medium by an absorption length of the shockwave medium.

16. The apparatus of claim 9, further comprising a controller configured to actuate the acoustic-wave generator to emit the sinusoidal acoustic waves in a periodic on-off sequence.

17. The apparatus of claim 9, wherein:

the shockwave medium occupies all of a cavity defined by the shockwave housing; and the at least one region of heterogeneity includes tattoo pigment particles or the at least one cellular structure comprises fat cells.

18. A method comprising:

forming unfocused shock waves by propagating sinusoidal acoustic waves having a frequency between 1 MHz and 1000 MHz through a shockwave medium disposed in and contained by a shockwave housing, the shockwave medium configured to exhibit nonlinear properties in the presence of the propagated sinusoidal acoustic waves; and delivering the unfocused shock waves formed by said propagation and exiting a distal end of the shockwave housing to a first region having at least one cellular structure comprising at least one region of heterogeneity and at least one homogeneous media; and rupturing the at least one cellular structure by using the unfocused shock waves.

19. The method of claim 18, wherein: the sinusoidal acoustic waves are generated at a proximal end of the shockwave housing; the proximal end of the shockwave housing is opposite the distal end of the shockwave housing; and the unfocused shockwaves are formed without focusing the acoustic waves.

20. The method of claim 18, further comprising the step of actuating a first acoustic wave generator to provide the sinusoidal acoustic waves and wherein delivering the unfocused shock waves to the first region does not rupture the at least one homogeneous media.

* * * * *